(12) United States Patent
Blinkovsky et al.

(10) Patent No.: US 6,465,209 B1
(45) Date of Patent: Oct. 15, 2002

(54) METHODS OF PRODUCING PROTEIN HYDROLYSATES

(75) Inventors: Alexander Blinkovsky, Davis; Kimberly Brown, Elk Grove; Elizabeth Golightly; Tony Byun, both of Davis, all of CA (US); Thomas E. Mathiasen, Copenhagen; Lene V. Kofod, Uggeløse, both of (DK); Mikio Fujii; Chigusa Marumoto, both of Shizuoka (JP)

(73) Assignees: Novozymes Biotech, Inc., Davis, CA (US); Novozymes A/S, Bagsvaerd (DK); Japan Tobacco, Inc., Tokyo (JP)

( * ) Notice: Subject to any disclaimer, the term of this patent is extended or adjusted under 35 U.S.C. 154(b) by 0 days.

(21) Appl. No.: 09/079,955

(22) Filed: May 15, 1998

Related U.S. Application Data

(63) Continuation-in-part of application No. 08/857,886, filed on May 16, 1997, now abandoned.
(60) Provisional application No. 60/069,719, filed on Dec. 16, 1997, and provisional application No. 60/062,893, filed on Oct. 20, 1997.

(30) Foreign Application Priority Data

Dec. 16, 1997 (DK) .............................................. 1465/97

(51) Int. Cl.[7] ............................ C12P 21/06; C12P 21/04
(52) U.S. Cl. ...................... 435/68.1; 435/71.1; 435/71.2
(58) Field of Search ............................... 435/68.1, 71.1, 435/71.2

(56) References Cited

U.S. PATENT DOCUMENTS 3,957,581 A * 5/1976 Tobe et al.

FOREIGN PATENT DOCUMENTS

| DE | 195 26 485 A1 | 1/1997 |
| EP | 0 578 572 A1 | 1/1994 |
| JP | 730358459 | 10/1973 |
| JP | 7115964 | 5/1995 |
| WO | WO 91/13554 | 9/1991 |
| WO | WO 94/25580 | 11/1994 |

* cited by examiner

*Primary Examiner*—Mark Navarro
(74) *Attorney, Agent, or Firm*—Robert Starnes; Elias Lambiris, Esq.

(57) ABSTRACT

The present invention relates to methods of producing protein hydrolysates, comprising adding to a proteinaceous material one or more aminopeptidase(s) having glycine releasing properties and one or more additional proteases wherein the amount of glycine produced is greater than the amount of glycine produced by the one or more additional proteases alone under the same conditions.

24 Claims, 12 Drawing Sheets

```
ATGAGGTCGCTTTTGTGGGCTTCGTTGCTTTCGGGCGTGTTGGCTGGGAGGGCGCTTGTTTCGCCGGATGAGTTCCCCGAGGATATTCAG  90
 M  R  S  L  L  W  A  S  L  L  S  G  V  L  A  G  R  A  L  V  S  P  D  E  F  P  E  D  I  Q

TTGGAAGATCTGCTGGAAGGATCCCAACAGCTTGAGGACTTCGCCTATGCCTACCCCGAGCGCAATCGCGTCTTTGGTGGTAAAGCCCAC 180
 L  E  D  L  L  E  G  S  Q  Q  L  E  D  F  A  Y  A  Y  P  E  R  N  R  V  F  G  G  K  A  H

GACGACACGGTTAACTATCTCTACGAGGAGCTGAAGAAGACTGGCTACTATGATGTCTACAAGCAGCCTCAGGTGCACCTGTGGAGCAAT 270
 D  D  T  V  N  Y  L  Y  E  E  L  K  K  T  G  Y  Y  D  V  Y  K  Q  P  Q  V  H  L  W  S  N

GCCGACCAGACGCTCAAGGTGGGCGATGAGGAAATCGAGGCGAAGACCATGACCTACAGTCCCAGCGTCGAGGTCACCGCCGATGTAGCC 360
 A  D  Q  T  L  K  V  G  D  E  E  I  E  A  K  T  M  T  Y  S  P  S  V  E  V  T  A  D  V  A

GTCGTCAAGAACCTGGGATGCAGCGAGGCGGATTACCCCATCCGATGTCGAGGGCAAGGTCGCCCTGATCAAGCGTGGAGAATGCCCGTTC 450
 V  V  K  N  L  G  C  S  E  A  D  Y  P  S  D  V  E  G  K  V  A  L  I  K  R  G  E  C  P  F

GGCGACAAGTCGGTTCTCGCTGCCAAAGCCAAGGCCGCGGCTTCGATTGTCTATAACAATGTGGCCGGATCCATGGCGGGCACCCTTGGC 540
 G  D  K  S  V  L  A  A  K  A  K  A  A  A  S  I  V  Y  N  N  V  A  G  S  M  A  G  T  L  G

GCGGCGCAGAGTGATAAGGGACCGTATTCGGCCATTGTCGGTATCAGCTTGGAGGATGGCCAGAAGCTGATCAAGCTTGCTGAGGCTGGA 630
 A  A  Q  S  D  K  G  P  Y  S  A  I  V  G  I  S  L  E  D  G  Q  K  L  I  K  L  A  E  A  G

TCGGTATCTGTGGATCTGTGGGTGGATAGTAAGCAGGAGAACCGTACGACGTATAACGTTGTCGCGCAGACGAAGGGCGGCGATCCGAAC 720
 S  V  S  V  D  L  W  V  D  S  K  Q  E  N  R  T  T  Y  N  V  V  A  Q  T  K  G  G  D  P  N

AACGTCGTCGCGCTGGGTGGCCACACGGACTCAGTCGAGGCGGGCCCTGGTATCAACGACGATGGCTCGGGCATTATTAGCAACTTGGTC 810
 N  V  V  A  L  G  G  H  T  D  S  V  E  A  G  P  G  I  N  D  D  G  S  G  I  I  S  N  L  V

ATTGCCAAAGCGCTCACGCAGTACTCCGTCAAGAATGCCGTGCGCTTCCTCTTCTGGACAGCAGAGGAGTTCGGTCTGCTGGGCAGCAAC 900
 I  A  K  A  L  T  Q  Y  S  V  K  N  A  V  R  F  L  F  W  T  A  E  E  F  G  L  L  G  S  N

TACTACGTCTCCCATCTGAATGCCACCGAGCTGAACAAGATCCGACTGTACCTGAACTTCGACATGATCGCCTCACCTAACTACGCCCTC 990
 Y  Y  V  S  H  L  N  A  T  E  L  N  K  I  R  L  Y  L  N  F  D  M  I  A  S  P  N  Y  A  L

ATGATCTATGACGGTGATGGATCGGCGTTCAACCAGAGCGGACCGGCCGGTTCCGCCCAGATCGAGAAACTGTTCGAGGACTACTACGAC 1080
 M  I  Y  D  G  D  G  S  A  F  N  Q  S  G  P  A  G  S  A  Q  I  E  K  L  F  E  D  Y  Y  D

TCCATCGACCTGCCTCATATCCCCACCCAGTTTGACGGACGTTCCGACTACGAGGCCTTTATCCTGAACGGCATTCCGTCCGGTGGACTC 1170
 S  I  D  L  P  H  I  P  T  Q  F  D  G  R  S  D  Y  E  A  F  I  L  N  G  I  P  S  G  G  L

TTCACGGGCGCCGAGGGCATCATGTCCGAAGAGAACGCAAGCCGCTGGGGAGGTCAAGCCGGCGTGGCCTACGACGCCAACTACCACGCC 1260
 F  T  G  A  E  G  I  M  S  E  E  N  A  S  R  W  G  G  Q  A  G  V  A  Y  D  A  N  Y  H  A

GCGGGAGACAACATGACCAACCTCAACCATGAAGCCTTCCTGATCAACTCCAAAGCCACCGCCTTCGCCGTCGCCACCTACGCCAACGAC 1350
 A  G  D  N  M  T  N  L  N  H  E  A  F  L  I  N  S  K  A  T  A  F  A  V  A  T  Y  A  N  D

CTCTCCTCGATCCCCAAACGGAATACCACATCCTCCTTGCACCGACGAGCCCGCACCATGCGACCATTCGGCAAGAGAGCTCCGAAGACA 1440
 L  S  S  I  P  K  R  N  T  T  S  S  L  H  R  R  A  R  T  M  R  P  F  G  K  R  A  P  K  T

CACGCTCACGTATCAGGATCCGGATGCTGGCATTCTCAAGTCGAGGCATAG 1491
 H  A  H  V  S  G  S  G  C  W  H  S  Q  V  E  A
```

METHODS OF PRODUCING PROTEIN HYDROLYSATES

CROSS-REFERENCE TO RELATED APPLICATIONS

This application is a continuation-in-part of U.S. application Ser. No. 08/857,886 filed May 16, 1997, now abandoned and claims priority of Danish application no. 1465/97 filed Dec. 16, 1997, and U.S. provisional application nos. 60/062,893 and 60/069,719 filed Oct. 20, 1997 and Dec. 16, 1997, respectively, which applications are fully incorporated herein by reference.

BACKGROUND OF THE INVENTION

1. Field of the Invention

The present invention relates to methods of producing a protein hydrolysate, comprising adding to a proteinaceous material one or more polypeptide(s) having glycine releasing activity and one or more additional proteases wherein the amount of glycine produced is greater than the amount of glycine produced by the one or more additional proteases alone under the same conditions.

2. Description of the Related Art

Various food products, e.g., soups, sauces and seasonings, contain flavoring agents obtained by hydrolysis of proteinaceous materials. This hydrolysis is conventionally accomplished using strong hydrochloric acid, followed by neutralization with sodium hydroxide. However, such chemical hydrolysis leads to severe degradation of the amino acids obtained during the hydrolysis, and also to hazardous byproducts formed in the course of this chemical reaction. Increasing concern over the use of flavoring agents obtained by chemical hydrolysis has led to the development of enzymatic hydrolysis processes.

Enzymatic hydrolysis processes of proteinaceous materials aim at obtaining a high degree of hydrolysis (DH), and this is usually attained using a complex of unspecific acting proteolytic enzymes (i.e., unspecific-acting endo- and exo-peptidases). For example, WO 94/25580 describes a method for hydrolyzing proteins by use of an unspecific acting enzyme preparation obtained from *Aspergillus oryzae*. Specific acting proteolytic enzymes have not been used for this purpose because such enzymes only lead to an inadequate degree of hydrolysis.

Polypeptides having aminopeptidase activity catalyze the removal of one or more amino acid residues from the N-terminus of peptides, polypeptides, and proteins. Such polypeptides are classified under the Enzyme Classification Number E.C. 3.4.11.- of the International Union of Biochemistry and Molecular Biology.

WO 96/28542 discloses an aminopeptidase which has a moleculer weight of 35 kDa. JP-7-5034631 (Noda) discloses a leucine aminopeptidase obtained from yellow koji mold, which includes *Aspergillus oryzae*. JP-7-4021798 (Zaidan Hojin Noda Sangyo) discloses the production of miso by adding a leucine aminopeptidase II prepared by cultivating a number of strains, including *Aspergillus oryzae* strain 460 (ATCC 20386) and strain IAM 2616. *Aspergillus oryzae* strain 460 is known to produce a number of leucine aminopeptidases of which three have a molecular weight of 26.5, 56, and 61 kDa by gel filtration (Nakada et al., 1972, *Agricultural and Biological Chemistry* 37: 757–765; Nakada et al., 1972, *Agricultural and Biological Chemistry* 37: 767–774; and Nakada et al., 1972, *Agricultural and Biological Chemistry* 37: 775–782; respectively). *Penicillium citrium* produces an intracellular leucine aminopeptidase with a molecular weight of 65 kDa by SDS-PAGE (Kwon et al., 1996, *Journal of Industrial Microbiology* 17: 30–35).

WO 97/04108 (Roehm) discloses DNA encoding an *Aspergillus sojae* leucine aminopeptidase. Chang and Smith (1989, *Journal of Biological Chemistry* 264: 6979–6983) disclose the molecular cloning and sequencing of a gene encoding a vacuolar aminopeptidase from *Saccharomyces cerevisiae*. Chang et al. (1992, *Journal of Biological Chemistry* 267: 8007–8011) disclose the molecular cloning and sequencing of a gene encoding a methionine aminopeptidase from *Saccharomycse cerevisiae*.

The production of protein hydrolysates with desirable organoleptic properties and high degrees of hydrolysis generally requires the use of a mixture of peptidase activities. It would be desirable to provide a single component peptidase enzyme which has activity useful for improving the organoleptic properties and degree of hydrolysis of protein hydrolysates used in food products either alone or in combination with other enzymes.

It is an object of the present invention to provide improved methods for producing protein hydrolysates with desirable organoleptic qualities and/or high degrees of hydrolysis.

SUMMARY OF THE INVENTION

The present invention relates to method of producing a protein hydrolysate, comprising adding to a proteinaceous material one or more aminopeptidase(s) having glycine releasing properties and one or more additional proteases wherein the amount of glycine produced is greater than the amount of glycine produced by the one or more additional proteases alone under the same conditions.

BRIEF DESCRIPTION OF THE FIGURES

FIG. 1 shows the nucleic acid sequence and the deduced amino acid sequence of an *Aspergillus oryzae* ATCC 20386 aminopeptidase (SEQ ID NOS:1 and 2, respectively).

DETAILED DESCRIPTION OF THE INVENTION

Figure 2:
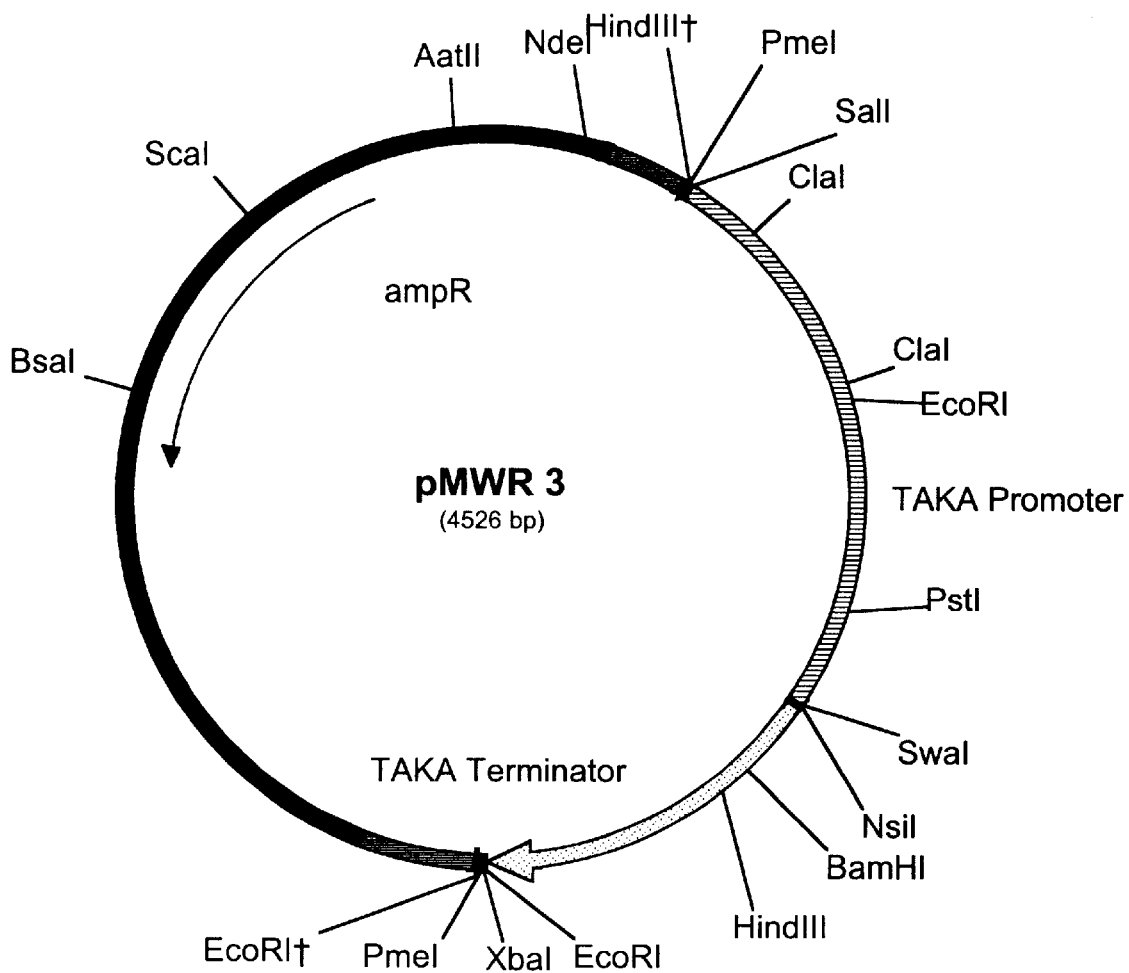
FIG. 2 shows a restriction map of pMWR3.

The present invention relates to method of producing a protein hydrolysate, comprising adding to a proteinaceous material one or more polypeptide(s) having glycine releasing activity and one or more additional proteases wherein the amount of glycine produced is greater than the amount of glycine produced by the one or more additional proteases alone under the same conditions. Because of the activity of the glycine-releasing polypeptide, the methods of the present invention are able to produce protein hydrolysates having a higher degree of hydrolysis or the same degree of hydrolysis using lower amounts of enzyme.

In a preferred embodiment, the amount of glycine produced is between 10–400%, preferably 50–350%, more preferably 100–350%, even more preferably 150–350%, and most preferably 200–350%, than the amount of glycine produced by the one or more additional proteases under the same conditions.

The enzymatic treatment(s) may take place at any convenient temperature at which the enzymes do not become inactivated, preferably in the range of from about 20° C. to about 70° C. In accordance with established practice, the enzymes may be inactivated by increasing the temperature of the incubation mixture to a temperature where the enzymes become inactivated, e.g., to above about 70° C., or by decreasing the pH of the incubation mixture to a point where the enzymes become inactivated, e.g., below about 4.0.

In a preferred embodiment, the methods of the present invention produce a protein hydrolysate having a degree of hydrolysis between 35–90%, preferably 45–80%, more preferably 50–75%, even more preferably 55–75%, and most preferably 60–70%.

The degree of hydrolysis (DH) is the percentage of the total number of amino bonds in a protein that has been hydrolyzed by a proteolytic enzyme. The DH is defined by the following formula:

$$DH = \frac{\text{Number of peptide bonds cleaved}}{\text{Total number of peptide bonds}} \times 100\%$$

The DH may be calculated according to Adler-Nissen; Enzymic Hydrolysis of Food Proteins; Elsvier Applied Science Publishers Ltd. (1986), page 122.

Proteinacous Material

The methods of the present invention comprise treating a proteinaceous material with at least two enzymes. The proteinaceous material may consist of intact proteins, prehydrolyzed proteins (i.e., peptides), or a mixture thereof.

In a preferred embodiment, the proteinaceous material is a foodstuff. The proteinaceous material may be of vegetable or animal origin.

In another preferred embodiment, the proteinaceous material is of animal origin, preferably milk protein, whey protein, casein, meat protein, fish protein, blood protein, egg white gelatin, or lactoalbumin.

In another preferred embodiment, the proteinaceous material is of vegetable origin, preferably soy protein, grain proteins, e.g., wheat gluten, corn gluten, barley, rye, oat, rice, zein, lupine, cotton seed protein, rape seed protein, peanut, alfalfa protein, pea protein, fabaceous bean protein, sesame seed protein, or sunflower.

Polypeptides Having Glycine Releasing Activity

One of the enzymes added to the proteinaceous material is a polypeptide having glycine releasing activity. The term "glycine releasing activity" is defined herein as a peptidase activity which catalyzes the removal of glycine from the N-terminal end of peptides, oligopeptides or proteins. The polypeptides may also have peptidase activity which is capable of cleaving one or more amino acids X from the N-terminus of a peptide, polypeptide, or protein, wherein X represents any amino acid residue selected from the group consisting of Ala, Arg, Asn, Asp, Cys, Gln, Glu, His, Ile, Leu, Lys, Met, Phe, Pro, Ser, Thr, Trp, Tyr, and Val, but at least Leu, Glu, Gly, Ala, and/or Pro.

The polypeptide(s) may be added to the proteinaceous substrate in an effective amount conventionally employed in protein hydrolysis processes, preferably in the range of from about 0.1 to about 100,000 aminopeptidase units per 100 g of protein, and more preferably in the range of from about 1 to about 10,000 aminopeptidase units per 100 g of protein. As defined herein, one aminopeptidase unit (APU) is the amount of enzyme needed to release 1 micromole of p-nitroanilide per minute from Leu-p-nitroanilide (Sigma Chemical Co., St. Louis Mo.) under the specified conditions. Alternatively, the aminopeptidase may be employed preferably in the range of from about 0.5 to about 500 LAPU/g of protein, and more preferably in the range of from about 5 to about 50 LAPU/g of protein. LAPU is defined as the leucine aminopeptidase activity which is determined as described in AF 298/1-GB (available on request from Novo Nordisk A/S, Denmark).

In a preferred embodiment, the polypeptide preferentially cleaves glycine.

In another preferred embodiment, the polypeptide is selected from the group consisting of:

(a) a polypeptide having an amino acid sequence which has at least 50% identity with the amino acid sequence of SEQ ID NO:2;

(b) a polypeptide encoded by a nucleic acid sequence which hybridizes under medium stringency conditions with (i) the nucleic acid sequence of SEQ ID NO:1, (ii) its complementary strand, or (iii) a subsequence thereof;

(c) an allelic variant of (a) or (b); and (d) a fragment of (a), (b), or (c), wherein the fragment has aminopeptidase activity; and (e) a polypeptide having aminopeptidase activity with physicochemical properties of (i) a pH optimum in the range of from about pH 7.27 to about pH 10.95 determined at ambient temperature in the presence of Ala-para-nitroanilide; (ii) a temperature stability of 90% or more, relative to initial activity, at pH 7.5 determined after incubation for 20 minutes at 60° C. in the absence of substrate; and (iii) an activity towards Xaa-para-nitroanilide wherein Xaa is selected from the group consisting of Leu, Glu, Gly, Ala, and Pro.

In another preferred embodiment, the polypeptide is selected from the group consisting of:

(a) a polypeptide having an amino acid sequence which has at least 50% identity with the amino acid sequence of SEQ ID NO:11;

(b) a polypeptide encoded by a nucleic acid sequence which hybridizes under medium stringency conditions with (i) the nucleic acid sequence of SEQ ID NO:10, (ii) its complementary strand, or (iii) a subsequence thereof;

(c) an allelic variant of (a) or (b); and (d) a fragment of (a), (b), or (c), wherein the fragment has aminopeptidase activity; and (e) a polypeptide which (a) has aminopeptidase activity in the pH range between pH 5.0–8.5 measured at 37° C., (b) an isoelectric point (pI) in the range of 7.4–8.5; (c) has aminopeptidase activity in the temperature range of 20–55° C., measured at pH 7.5 using Gly-pNA in Tris-HCl buffer; (d) hydrolyzes Ala-pNA, Gly-pNA, Leu-pNA, Glu-pNA, Asp-pNA, Lys-pNA, Ile-pNA and Val-pNA; (e) does not hydrolyze Phe-pNA nor Pro-pNA; (f) is not inhibited by phenylmethanesulfonyl fluoride, slightly inhibited by EDTA, di-isopropyl fluoro phosphate, p-chloromercuribenzoic acid and iodoacetic acid, completely inhibited by o-phenanthrolin, and/or (g) is obtained from a strain belonging to Sphingomonas and has a molecular mass of 67±5 kDa.

In a preferred embodiment, the polypeptide has an amino acid sequence which has a degree of identity to the amino acid sequence of SEQ ID NO:2 or 11 of at least about 50%, preferably at least about 60%, preferably at least about 70%, more preferably at least about 80%, even more preferably at least about 90%, most preferably at least about 95%, and even most preferably at least about 97%, which have aminopeptidase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from the amino acid sequence of SEQ ID NO:2 or 11. For purposes of the present invention, the degree of identity between two amino acid sequences is determined by the Clustal method (Higgins, 1989, *CABIOS* 5: 151–153) with an identity table, a gap penalty of 10, and a gap length penalty of 10.

Preferably, the polypeptides comprise the amino acid sequence of SEQ ID NO:2 or 11, an allelic variant; and a fragment thereof, wherein the fragment has aminopeptidase activity. In a more preferred embodiment, the polypeptides comprise the amino acid sequence of SEQ ID NO:2 or 11. In another preferred embodiment, the polypeptide has the amino acid sequence of SEQ ID NO:2 or 11 or a fragment thereof, wherein the fragment has aminopeptidase activity. A fragment of SEQ ID NO:2 is a polypeptide having one or more amino acids deleted from the amino and/or carboxy terminus of this amino acid sequence. In a most preferred embodiment, the polypeptide has the amino acid sequence of SEQ ID NO:2 or 11.

Preferably, a fragment contains at least 330 amino acid residues, more preferably at least 380 amino acid residues, and most preferably at least 430 amino acid residues.

An allelic variant denotes any of two or more alternative forms of a gene occupying the same chomosomal locus. Allelic variation arises naturally through mutation, and may result in phenotypic polymorphism within populations. Gene mutations can be silent (no change in the encoded polypeptide) or may encode polypeptides having altered amino acid sequences. The term allelic variant is also used to denote a protein encoded by an allelic variant of a gene.

The amino acid sequences of the homologous polypeptides may differ from the amino acid sequence of SEQ ID NO:2 or 11 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (such as arginine, lysine and histidine), acidic amino acids (such as glutamic acid and aspartic acid), polar amino acids (such as glutamine and asparagine), hydrophobic amino acids (such as leucine, isoleucine and valine), aromatic amino acids (such as phenylalanine, tryptophan and tyrosine), and small amino acids (such as glycine, alanine, serine, threonine and methionine). Amino acid substitutions which do not generally alter the specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In another preferred embodiment, the polypeptide are encoded by nucleic acid sequences which hybridize under low stringency conditions, more preferably medium stringency conditions, and most preferably high stringency conditions, with an oligonucleotide probe which hybridizes under the same conditions with the nucleic acid sequence of SEQ ID NO:1 or 10 or their complementary strand (J. Sambrook, E. F. Fritsch, and T. Maniatus, 1989, *Molecular Cloning, A Laboratory Manual*, 2d edition, Cold Spring Harbor, New York); or allelic variants and fragments of the polypeptides, wherein the fragments have aminopeptidase activity.

Hybridization indicates that the nucleic acid sequence hybridizes to the oligonucleotide probe corresponding to the polypeptide encoding part of the nucleic acid sequence shown in SEQ ID NO:1 or 10, under low to high stringency conditions (i.e., prehybridization and hybridization at 42° C. in 5×SSPE, 0.3% SDS, 200 μg/ml sheared and denatured salmon sperm DNA, and either 25, 35 or 50% formamide for low, medium and high stringencies, respectively), following standard Southern blotting procedures.

The amino acid sequence of SEQ ID NO:2 or 11 or a partial sequence thereof may be used to design an oligonucleotide probe, or a nucleic acid sequence encoding a polypeptide of the present invention, such as the nucleic acid sequence of SEQ ID NO:1 or 10, or a subsequence thereof, may be used to identify and clone DNA encoding polypeptides having aminopeptidase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 40 nucleotides in length. Longer probes can also be used. Both DNA and RNA probes can be used. The probes are typically labeled for detecting the corresponding gene (for example, with $^{32}P$, $^{3}H$, $^{35}S$, biotin, or avidin).

Thus, a genomic, cDNA or combinatorial chemical library prepared from such other organisms may be screened for DNA which hybridizes with the probes described above and which encodes a polypeptide having aminopeptidase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO:1 or 10, the carrier material is used in a Southern blot in which the carrier material is finally washed three times for 30 minutes each using 2×SSC, 0.2% SDS preferably at least 50° C., more preferably at least 55° C., more preferably at least 60° C., more preferably at least 65° C., even more preferably at least 70° C., and most preferably at least 75° C. Molecules to which the oligonucleotide probe hybridizes under these conditions are detected using X-ray film.

In another preferred embodiment, the polypeptides have the following physicochemical properties: (a) a pH optimum in the range of from about pH 7.27 to about pH 10.95 determined at ambient temperature in the presence of Ala-para-nitroanilide; (ii) a temperature stability of 90% or more, relative to initial activity, at pH 7.5 determined after incubation for 20 minutes at 60° C. in the absence of substrate; and (iii) an activity towards Xaa-para-nitroanilide wherein Xaa is selected from the group consisting of Leu, Glu, Gly, Ala, and Pro. The polypeptides also have the ability to hydrolyze other substrates.

In a preferred embodiment, the pH optimum in the range of from about pH 7.27 to about pH 10.95, more preferably in the range of from about pH 8.03 to about pH 10.95, and most preferably in the range of from about pH 8.62 to about pH 10.51 determined after incubation for 5 minutes at ambient temperature in the presence of Ala-Pro-para-nitroanilide.

In another preferred embodiment, the polypeptide has a molecular mass of 67±5 kDa, more preferably a molecular mass of 67±2 kDa and is obtained from a strain belonging to Sphingomonas, more preferably *Sphingomonas capsulata* and most preferably *Sphingomonas capsulata* IFO 12533. The molecular mass is measured by SDS-polyacrylamide gel electrophoresis (SDS-PAGE) using a 10–15% gradient gel on the apparatus of FAST System from Pharmacia (Uppsala, Sweden). The molecular mass of the enzyme was estimated from the regression line of molecular weight markers as follows:

phosphorylase b (94 kDa)

albumin (67 kDa)

ovalbumin (43 kDa)

carbonic anhydrase (30 kDa)

trypsine inhibitor (20.1 kDa)

a-lactalbumine (14.4 kDa)

In another preferred embodiment, the polypeptide (a) has aminopeptidase activity in the pH range between pH 5.0–8.5 measured at 37° C., more preferably in the pH range 6.5–8.0, and even more preferably having the highest aminopeptidase activity in the pH range 7.0–7.5 measured at 37° C.; (b) an isoelectric point (pI) in the range of 7.4–8.5; (c) has aminopeptidase activity in the temperature range of 20–55° C., measured at pH 7.5 using Gly-pNA in Tris-HCl buffer; (d) hydrolyzes Ala-pNA, Gly-pNA, Leu-pNA, Glu-pNA, Asp-pNA, Lys-pNA, Ile-pNA and Val-pNA; (e) does not hydrolyze Phe-pNA nor Pro-pNA; and/or (f) is not inhibited by phenylmethanesulfonyl fluoride, slightly inhibited by EDTA, di-isopropyl fluoro phosphate, p-chloromercuribenzoic acid and iodoacetic acid, completely inhibited by o-phenanthrolin.

The isoelectric point of the aminopeptidase is variable since the pI of the freshly prepared enzyme is estimated as 8.4 using an activity staining method, however, pI varies to 7.4–8.5 during the course of purification and/or storage. The uncertainty of pI may be due to the self digestion of the aminopeptidase from its amino terminal.

In a more preferred embodiment, the polypeptide is obtained from an *Aspergillus oryzae* strain, and most preferably from *Aspergillus oryzae* ATCC 20386 or a mutant strain thereof, e.g., the polypeptide with the amino acid sequence of SEQ ID NO:2.

In another preferred embodiment, the polypeptide is obtained from a *Sphingomonas capsulata* strain, e.g., *Sphingomonas capsulata* is IFO 12533, which is a bacterial strain kept at the Institute for Fermentation, Osaka, Japan, e.g., the polypeptide with the amino acid sequence of SEQ ID NO:11 (the predicted signal peptide consists of the first 32 amino acids).

In another embodiment, the polypeptides have immunochemical identity or partial immunochemical identity to the polypeptide having the amino acid sequence of SEQ ID NO:2 or 11. The immunochemical properties are determined by immunological cross-reaction identity tests by the well-known Ouchterlony double immunodiffusion procedure. Specifically, an antiserum containing antibodies which are immunoreactive or bind to epitopes of the polypeptide having the amino acid sequence of SEQ ID NO:2 or 11 are prepared by immunizing rabbits (or other rodents) according to the procedure described by Harboe and Ingild, In N. H. Axelsen, J. Krøll, and B. Weeks, editors, *A Manual of Quantitative Immunoelectrophoresis*, Blackwell Scientific Publications, 1973, Chapter 23, or Johnstone and Thorpe, *Immunochemistry in Practice*, Blackwell Scientific Publications, 1982 (more specifically pages 27–31). A polypeptide having immunochemical identity is a polypeptide which reacts with the antiserum in an identical fashion such as total fusion of precipitates, identical precipitate morphology, and/or identical electrophoretic mobility using a specific immunochemical technique. A further explanation of immunochemical identity is described by Axelsen, Bock, and Krøll, In N. H. Axelsen, J. Kroll, and B. Weeks, editors, *A Manual of Quantitative Immunoelectrophoresis*, Blackwell Scientific Publications, 1973, Chapter 10. A polypeptide having partial immunochemical identity is a polypeptide which reacts with the antiserum in a partially identical fashion such as partial fusion of precipitates, partially identical precipitate morphology, and/or partially identical electrophoretic mobility using a specific immunochemical technique. A further explanation of partial immunochemical identity is described by Bock and Axelsen, In N. H. Axelsen, J. Krøll, and B. Weeks, editors, *A Manual of Quantitative Immunoelectrophoresis*, Blackwell Scientific Publications, 1973, Chapter 11.

Polypeptides encoded by nucleic acid sequences which hybridize with an oligonucleotide probe which hybridizes with the nucleic acid sequence of SEQ ID NO:1 or 10, their complementary strands, or allelic variants and subsequences of SEQ ID NO:1 or 10; allelic variants and fragments of the polypeptides; or the homologous polypeptides and polypeptides having identical or partially identical immunological properties may be obtained from microorganisms of any genus.

In a preferred embodiment, these polypeptides may be obtained from a bacterial source. For example, these polypeptides may be obtained from a gram positive bacterium such as a Bacillus strain, e.g., *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* or *Bacillus thuringiensis*; or a Streptomyces strain, e.g., *Streptomyces liv-*

*idans* or *Streptomyces murinus*; or from a gram negative bacterium, e.g., *E. coli* or *Pseudomonas* sp.

The polypeptides may be obtained from a fungal source, and more preferably from a yeast strain such as a Candida, Kluyveromyces, Pichia, Saccharomyces, Schizosaccharomyces, or Yarrowia strain; or a filamentous fungal strain such as an Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium, or Trichoderma strain.

In a preferred embodiment, the polypeptides are obtained from a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* strain.

In another preferred embodiment, the polypeptides are obtained from a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei,* or *Trichoderma viride* strain.

The polypeptides are preferably obtained from species of Aspergillus including, but not limited to, *Aspergillus aculeatus, Aspergillus awamori, Aspergillus foetidus, Aspergillus japonicus, Aspergillus nidulans, Aspergillus niger,* or *Aspergillus oryzae.*

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents. The polypeptides may also be obtained from microorganisms which are synonyms of Aspergillus as defined by Raper, K. D. and Fennel, D. I., 1965, The Genus Aspergillus, The Wilkins Company, Baltimore. Aspergilli are mitosporic fungi characterized by an aspergillum comprised of a conidiospore stipe with no known teleomorphic states terminating in a vesicle, which in turn bears one or two layers of synchronously formed specialized cells, variously referred to as sterigmata or phialides, and asexually formed spores referred to as conidia. Known teleomorphs of Aspergillus include Eurotium, Neosartorya, and Emericella. Strains of Aspergillus and teleomorphs thereof are readily accessible to the public in a number of culture collections, such as the American Type Culture Collection (ATCC), Deutsche Sammlung von Mikroorganismen und Zellkulturen GmbH (DSM), Centraalbureau Voor Schimmnelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding the polypeptide has been detected with the probe(s), the sequence may be isolated or cloned by utilizing techniques which are known to those of ordinary skill in the art (see, e.g., Sambrook et al., 1989, supra).

For purposes of the present invention, the term "obtained from" as used herein in connection with a given source shall mean that the polypeptide is produced by the source or by a cell in which a gene from the source has been inserted.

The polypeptide(s) may be a fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Additional Protease(s)

In the methods of the present invention, the proteinaceous material also is treated with one or more additional proteases. The additional protease(s) may be added simultaneously with the polypeptide(s) or consecutively. The additional protease(s) may be added to the proteinaceous material in an effective amount conventionally employed in protein hydrolysis processes.

The one or more additional proteases may be endopeptidases. The endopeptidase(s) may be added to the proteinaceous substrate in an effective amount conventionally employed in protein hydrolysis processes, preferably in the range of from about 0.05 to about 15 AU/100 g of protein, and more preferably from about 0.1 to about 8 AU/100 g of protein. One AU (Anson Unit) is defined as the amount of enzyme which under standard conditions (i.e., 25° C., pH 7.5 and 10 min. reaction time) digests hemoglobin at an initial rate such that there is liberated per minute an amount of TCA soluble product which gives the same color with phenol reagent as one milli-equivalent of tyrosine. The analytical method AF 4/5 is available upon request from Novo Nordisk A/S, Denmark, which is incorporated herein by reference.

In a preferred embodiment, the endopeptidase is a glutamyl endopeptidase (EC 3.4.21.19); a lysyl endopeptidase (EC 3.4.21.50); a leucyl endopeptidase (EC 3.4.21.57); a glycyl endopeptidase (EC 3.4.22.25); a prolyl endopeptidase (EC 3.4.21.26); trypsin (EC 3.4.21.4) or a trypsin-like (lysine/arginine specific) endopeptidase; or a peptidyl-Asp metalloendopeptidase (EC 3.4.24.33).

The glutamyl endopeptidase (EC 3.4.21.19) may preferably be obtained from a Bacillus strain, in particular *Bacillus licheniformis* and *Bacillus subtilis*, a Staphylococcus strain, in particular *Staphylococcus aureus*, a Streptomyces strain, in particular *Streptomyces thenmovulgaris* and *Streptomyces griseus*, or a Actinomyces strain.

The lysyl endopeptidase (EC 3.4.21.50) may preferably be obtained from a Achromobacter strain, in particular *Achromobacter lyticus*, a Lysobacter strain, in particular *Lysobacter enzymogenes*, or a Pseudomonas strain, in particular *Pseudomonas aeruginosa.*

The leucyl endopeptidase (EC 3.4.21.57) may be of plant origin.

The glycyl endopeptidase (EC 3.4.22.25) may preferably be obtained from the papaya plant (*Carica papaya*).

The prolyl endopeptidase (EC 3.4.21.26) may preferably be obtained from a Flavobacterium strain, or it may be of plant origin.

The trypsin-like endopeptidase may preferably be obtained from a Fusarium strain, in particular *Fusarium oxysporum*, e.g., as described in WO 89/06270 or WO 94125583.

The peptidyl-Asp metalloendopeptidase (EC 3.4.24.33) may preferably be obtained from a Pseudomonas strain, in particular *Pseudomonas fragi*.

The endopeptidase may be obtained from a strain of Bacillus, preferably *Bacillus amyloliquefaciens, Bacillus lentus, Bacillus licheniformis* or *Bacillus subtilis*, a strain of Staphylococcus, preferably *Staphylococcus aureus*, a strain of Streptomyces, preferably *Streptomyces thermovularis* or *Streptomyces griseus*, a strain of Actinomyces species, a strain of Aspergillus, preferably *Aspergillus aculeatus, Aspergillus awamori, Aspergillus foetidus, Aspergillus nidulans, Aspergillus niger, Aspergillus oryzae*, or *Aspergillus sojae*, or a strain of Fusarium, preferably *Fusarium venenatum*.

In another preferred embodiment, the specific acting proteolytic enzyme is an exopeptidase that may act from either end of the peptide.

In a preferred embodiment, the exopeptidase is an aminopeptidase such as a leucyl aminopeptidase (EC 3.4.11.1); a dipeptide aminopeptidase or a tripeptide aminopeptidase (EC 3.4.11.4).

In another preferred embodiment, the exopeptidase is a carboxypeptidase such as a proline carboxypeptidase (EC 3.4.16.2); a carboxypeptidase A (EC 3.4.17.1); a carboxypeptidase B (EC 3.4.17.2); a carboxypeptidase C (EC 3.4.16.5); a carboxypeptidase D (EC 3.4.16.6); a lysine (arginine) carboxypeptidase (EC 3.4.17.3); a glycine carboxypeptidase (EC 3.4.17.4); an alanine carboxypeptidase (EC 3.4.17.6); a glutamate carboxypeptidase (EC 3.4.17.11); a peptidyl-dipeptidase A (EC 3.4.15.1); or a peptidyl-dipeptidase (EC 3.4.15.5).

In a most preferred embodiment, the additional protease is a plurality of proteases sold under the name FLAVOURZYME™ manufactured by Novo Nordisk A/S, Denmark. The protease formulation contains at least five *Aspergillus oryzae*-derived proteases and peptidases of different molecular weight.

Additional Enzymes

In a preferred embodiment, the proteinaceous material is treated with one or more additional enzymes. The one or more additional enzymes may be an amylase, carbohydrase, cellulase, esterase, alpha-galactosidase, beta-galactosidase, glucoamylase, alpha-glucosidase, beta-glucosidase, lipase, pectinolytic enzyme, peptidoglutaminase, phytase, transglutaminase, or xylanase.

The additional enzyme(s) may be obtained from a microorganism belonging to the genus Aspergillus, preferably *Aspergillus aculeatus, Aspergillus awamori, Aspergillus niger*, or *Aspergillus oryzae*, Trichoderma, Humicola, preferably *Humicola insolens*, or Fusarium, preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum*.

Protein Hydrolysates

The present invention also relates to protein hydrolysates produced by the methods of the present invention.

The present invention also relates to protein hydrolysates enriched in free glutamic acid and/or peptide bound glutamic acid residues. Such protein hydrolysates can be produced by subjecting the proteinaceous material to a deamidation process either prior to or simultaneously with the enzymatic treatment(s).

These protein hydrolysates have excellent flavor because glutamic acid (Glu), whether free or peptide bound, plays an important role in the flavor and palatability of protein hydrolysates. These protein hydrolysates also have improved functionality, in particular, improved solubility, improved emulsifying properties, increased degree of hydrolysis, and improved foaming properties.

The deamidation process, i.e., the conversion of amides (glutamine or asparagine) into charged acids (glutamic acid or aspartic acid) via the liberation of ammonia, may take place as a non-enzymatic or as an enzymatic deamidation process.

In a preferred embodiment, the deamidation is carried out as an enzymatic deamidation process, e.g., by subjecting the substrate to a transglutaminase and/or peptidoglutaminase.

The transglutaminase may be of any convenient source including mammals, see e.g., JP 1050382 and JP 5023182, including activated Factor XIII, see e.g., WO 93/15234; those derived from fish, see e.g., EP 555,649; and those obtained from microorganisms, see e.g., EP 379,606, WO 96/06931 and WO 96/22366. In a preferred embodiment, the transglutaminase is obtained from an Oomycete, including a strain of Phytophthora, preferably *Phytophthora cactorum*, or a strain of Pythium, preferably *Pythium irregulare, Pythium sp., Pythium intermedium, Pythium ultimum*, or *Pythium periilum* (or *Pythium periplocum*). In another preferred embodiment, the transglutaminase is of bacterial origin and is obtained from a strain of Bacillus, preferably *Bacillus subtilis*, a strain of Streptoverticillium, preferably *Streptoverticillium mobaraensis, Streptoverticillium griseocarneum*, or *Streptoverticillium cinnamoneum*, and a strain of Streptomyces, preferably *Streptomyces lydicus*.

The peptidoglutaminase may be a peptidoglutaminase I (peptidyl-glutaminase; EC 3.5.1.43), or a peptidoglutaminase II (protein-glutamine glutaminase; EC 3.5.1.44), or any mixture thereof. The peptidoglutaminase may be obtained from a strain of Aspergillus, preferably *Aspergillus japonicus*, a strain of Bacillus, preferably *Bacillus circulans*, a strain of Cryptococcus, preferably *Cryptococcus albidus*, or a strain of Debaryomyces, preferably *Debaryomyces kloecheri*.

The transglutaminase is added to the proteinaceous substrate in an effective amount conventionally employed in deamidation processes, preferably in the range of from about 0.01 to about 5% (w/w), and more preferably in the range of from about 0.1 to about 1% (w/w) of enzyme preparation relating to the amount of substrate.

The peptidoglutaminase is added to the proteinaceous substrate in an effective amount conventionally employed in deamidation processes, preferably in the range of from about 0.01 to about 100,000 PGase Units per 100 g of substrate, and more preferably in the range of from about 0.1 to about 10,000 PGase Units per 100 g of substrate.

The peptidoglutaminase activity may be determined according to the procedure of Cedrangoro et al. (1965, *Enzymologia* 29: 143). According to this procedure, 0.5 ml of an enzyme sample, adjusted to pH 6.5 with 1 N NaOH, is charged into a small vessel. Then 1 ml of a borate pH 10.8 buffer solution is added to the vessel. The discharged ammnonia is absorbed by 5 N sulphuric acid, and by use of Nessler's reagent the mixture is allowed to form color which is measured at 420 nm. One PGase unit is the amount of enzyme capable of producing 1 micromole of ammonia per minute under these conditions.

Alternatively, the peptidoglutaminase activity may be determined according to the procedure described in U.S. Pat. No. 3,857,967 or Example 20 below.

The present invention also relates to food products, e.g., baked products, and animal feed additives comprising a protein hydrolysate obtained by the methods of the present invention. Such food products exhibit enhanced organoleptic qualities, such as improvement in flavor, palatability, mouth feel, aroma and crust color.

In the present context, the term "baked products" includes any food prepared from dough, either of a soft or a crisp character. Examples of baked products, whether of a, white, light or dark type, which may be advantageously produced by the present invention, are bread, in particular white, whole-meal or rye bread, typically in the form of loaves or rolls; French baguette-type breads; pita breads; tacos; cakes; pancakes; biscuits; crisp breads; and the like.

Such baked products are conventionally prepared from a dough which comprises flour and water, and which is typically leavened. The dough may be leavened in various ways, such as by adding sodium bicarbonate or the like, or by adding a leaven (fermenting dough), but the dough is preferably leavened by adding a suitable yeast culture such as a culture of *Saccharomyces cerevisiae* (baker's yeast). Any of the commercially available *Saccharomyces cerevisiae* strains may be employed.

Further, the dough used in the preparation of the baked products may be fresh or frozen. The preparation of frozen dough is described by K. Kulp and K. Lorenz in "Frozen and Refrigerated Doughs and Batters". A flavor improving composition of the present invention is typically included in the dough in an amount in the range of 0.01–5%, more preferably 0.1–3%.

The present invention also relates to the use of a hydrolysate produced by the methods of the invention as an additive to food products, such as baked foods, to enhance organoleptic qualities, such as flavor, palatability and aroma.

The present invention is further described by the following examples which should not be construed as limiting the scope of the invention.

EXAMPLES

Example 1

Purification of FLAVOURZYME™ Aminopeptidase II

Aminopeptidase was purified from a FLAVOURZYME™ broth (Novo Nordisk A/S, Bagsvxrd, Denmark). The FLAVOURZYME™ broth was produced by cultivation of *Aspergillus oryzae* strain 1568 (ATCC 20386) in a medium composed of carbon and nitrogen sources and trace metals. First, the broth (20 ml containing 720 mg of protein) was diluted with 180 ml of 20 mM sodium phosphate pH 7.0 buffer and filtered using Nalgene Filterware equipped with a 0.45 μm filter (Nalgene, Rochester, N.Y.). The filtered solution was loaded onto a 24×130 mm column containing 31 ml of Q-Sepharose, Big Beads (Pharmacia Biotech AB, Uppsala, Sweden) pre-equilibrated with 20 mM sodium phosphate pH 7.0 buffer. The protein was eluted using pH gradients from 7.0 (20 mM sodium phosphate buffer) to 5.0 (20 mM sodium acetate buffer), from 5.0 to 3.5 (20 mM sodium acetate buffer), and then from 3.5 to 3.0 (20 mM sodium acetate buffer). Fractions eluting between pH 3.5 and 3.0 were collected, pooled, and concentrated to 20 ml by ultrafiltration with a PM 10 membrane (Amicon, New Bedford, Mass.).

The concentrated solution was diluted with 100 ml of 20 mM sodium phosphate pH 7.0 buffer and then loaded onto a 20 x 100 mm column containing Pharmacia MonoQ Beads (Pharmacia Biotech AB, Uppsala, Sweden) pre-equilibrated with 20 mM sodium phosphate pH 7.0 buffer. The protein was eluted with a 0 to 0.4 M NaCl gradient in 20 mM sodium phosphate pH 7.0 buffer. The fractions between 0.330 and 0.343 M NaCl were collected, pooled, and concentrated using ultrafiltration against 20 mM sodium acetate pH 4.0 buffer.

The purified preparation was found to contain three major bands judged by SDS-PAGE analysis. The sample consisted of components with molecular weights of approximately 65, 50 and 33 kDa.

Example 2

Amino Acid Sequencing of Aminopeptidase II

An aliquot of the purified aminopeptidase II preparation described in Example 1 was electrophoresed and subsequently blot-transferred to a PVDF membrane (Novex, San Diego, Calif.) using 10 mM CAPS (3-[cyclohexylamino]-1-propanesulfonic acid) pH 11 in 10% methanol for 2 hours. The PVDF membrane was stained with 0.1% Coommassie Blue R-250 in 40% methanol/1% acetic acid for 20 seconds and destained in 50% ethanol to observe the protein bands. Three components at 65, 50, and 33 kDa were excised and subjected to amino terminal sequencing on an Applied Biosystems Model 476A Protein Sequencer (Applied Biosystems, Inc., Foster City, Calif.) using a blot cartridge and liquid phase TFA delivery according to the manufacturer's instructions. All three components yielded the same amino terminal sequence, RALVSPDEFPEDIQLEDLLEG-SQQLEDFAY (SEQ ID NO:2).

A 300 μl sample of the protein was dried on a Savant Speed Vac AS160 (Savant Instruments, Farmingdale, N.Y.) and then reconstituted with 300 μl of 70% formic acid (aqueous). A few crystals of cyanogen bromide were added and incubated at room temperature in the dark overnight. The sample was redried in the Speed Vac and reconstituted in Tricine sample buffer (Novex, San Diego, Calif.). The cyanogen bromide cleavage fragments were separated using a 10–20% Tricine SDS-polyacrylamide gel into bands of 6, 10, 15, 22, 27, 40 and 50 kDa and blot-transferred to a PVDF membrane. The 6, 10, 15, and 22 kDa bands were excised and subjected to amino terminal sequencing.

The amino terminal sequences of the 15 and 22 kDa bands were identical to the amino terminal sequence above, while the sequences of the 6 and 10 kDa bands were both determined to contain the sequence TYSPSVEVTADVAVVKN-LGTSEADYPDVEGKVAL (SEQ ID NO:2).

Example 3

*Aspergillus oryzae* Strain 1568 RNA Isolation

*Aspergillus oryzae* strain 1568 was cultivated in a fermentation tank in a medium composed of 7.5 g of potato starch, 10 g of soy bean meal, 2 g of $KH_2PO_4$, 5 g of $Na_2HPO_4$-$2H_2O$, and 0.1 g of $ZnSO_4$-$7H_2O$ per liter. A two liter sample was taken after five days of growth at 30° C., and the mycelia were collected, frozen in liquid N$_2$, and stored at −80° C. Total RNA was prepared from the frozen, powdered mycelia of *Aspergillus oryzae* 1568 by extraction with guanidinium thiocyanate followed by ultracentrifugation through a 5.7 M cesium chloride cushion (Chirgwin et al., 1979, Biochemistry 18: 5294–5299). Poly(A)+ RNA was isolated by oligo(dT)-cellulose affinity chromatography according to Aviv and Leder (1972, *Proceedings of the National Academy of Sciences USA* 69: 1408–1412).

Example 4

Construction of a cDNA Library

Double-stranded cDNA was synthesized from 5 μg of *Aspergillus oryzae* 1568 poly(A)+ RNA of Example 3 using the procedure described by Gubler and Hoffman (1983, *Gene* 25: 263–269) and Sambrook et al. (1989, *Molecular Cloning: A Laboratory Manual*, Cold Spring Harbor Press, Cold Spring Harbor, New York), except that an oligo(dT)-NotI anchor primer, instead of an oligo(dT)12–18 primer, was used in the first strand reaction. After synthesis, the cDNA was treated with Mung bean nuclease (Life Technologies, Gaithersburg, Md.), blunt-ended with T4 DNA polymerase (Boehringer Mannheim, Indianapolis, Ind.), and ligated to non-palindromic BstXI adaptors (Invitrogen, San Diego, Calif.), using about 50-fold molar excess of the adaptors. The adapted cDNA was digested with NotI, size-fractionated for 1.2–3.0 kb cDNAs by agarose gel electrophoresis, and ligated into pYES2.0 (Invitrogen, San Diego, Calif.) cleaved with BstXI/NotI. The ligation mixture was transformed into electrocompetent *E. coli* DH10B cells (Life Technologies, Gaithersburg, Md.) according to the manufacturer's instructions. The library consisting of 1×10$^6$ independent clones was stored as individual pools (25,000–30,000 colony forming units/pool) in 20% glycerol at −80° C., and as double stranded cDNA and ligation mixture at −20° C.

Example 5

Genomic DNA Extraction

*Aspergillus oryzae* 1568 was grown in 25 ml of 0.5% yeast extract-2% glucose (YEG) medium for 24 hours at 37° C. and 250 rpm. Mycelia were then collected by filtration through Miracloth (Calbiochem, La Jolla, Calif.) and washed once with 25 ml of 10 mM Tris-1 mM EDTA (TE) buffer. Excess buffer was drained from the mycelia preparation which was subsequently frozen in liquid nitrogen. The frozen mycelia preparation was ground to a fine powder in an electric coffee grinder, and the powder was added to a disposable plastic centrifuge tube containing 20 ml of TE buffer and 5 ml of 20% w/v sodium dodecylsulfate (SDS). The mixture was gently inverted several times to ensure mixing, and extracted twice with an equal volume of phenol:chloroform:isoamyl alcohol (25:24:1 v/v/v). Sodium acetate (3 M solution) was added to the extracted sample to a final concentration of 0.3 M followed by 2.5 volumes of ice cold ethanol to precipitate the DNA. The tube was centrifuged at 15,000×g for 30 minutes to pellet the DNA. The DNA pellet was allowed to air-dry for 30 minutes before resuspension in 0.5 ml of TE buffer. DNase-free ribonuclease A was added to the resuspended DNA pellet to a concentration of 100 μg per ml and the mixture was then incubated at 37° C. for 30 minutes. Proteinase K (200 μg/ml) was added and the tube was incubated an additional one hour at 37° C. Finally, the sample was extracted twice with phenol:chloroform:isoamyl alcohol and the DNA precipitated with ethanol. The precipitated DNA was washed with 70% ethanol, dried under vacuum, resuspended in TE buffer, and stored at 4° C.

Example 6

PCR Amplification of *Aspergillus oryzae* 1568 Aminopeptidase II

Based on the amino acid sequences of the *Aspergillus oryzae* 1568 aminopeptidase II partial peptides described in Example 2, the degenerate oligonucleotide primers shown below were synthesized with an Applied Biosystems Model 394 DNA/RNA Synthesizer, according to the manufacturer's instructions, to PCR amplify aminopeptidase II gene fragments from *Aspergillus oryzae* 1568 genomic DNA.

Forward primer: 5'-CCIGAYGARTTYCCIGARGA-3' (SEQ ID NO:3)

Reverse primer: 5'-RTTYTTIACIACIGCIACRTCIG-CIGTIACYTCIAC-3' (SEQ ID NO:4)

(R=A or G, Y=C or T, N=G or A or C or T, H=A or C or T, I=Inosine)

Amplification reactions (50 μl) were prepared using approximately 1 μg of Aspergillus oryzae 1568 genomic DNA, prepared as described in Example 5, as the template. Each reaction contained the following components: 1 μg of genomic DNA, 40 pmol of the forward primer, 40 pmol of the reverse primer, 200 μM each of dATP, dCTP, dGTP, and dTTP, 1×Taq polymerase buffer (Perkin-Elmer Corp., Branchburg, N.J.), and 2.5 Units of Taq polymerase (Perkin-Elmer Corp., Branchburg, N.J.). The reactions were incubated in a Perkin-Elmer Model 480 Thermal Cycler programmed as follows: Cycle 1 at 94° C. for 5 minutes, 50° C. for 2 minutes, and 72° C. for 2 minutes; and Cycles 2–26 at 94° C. for 2 minutes, 50° C. for 1 minute, and 72° C. for 2 minutes. The reaction products were isolated on a 1.5% agarose gel (Eastman Kodak, Rochester, N.Y.) where a 309 bp product band was excised from the gel and purified using Qiaex II (Qiagen, Chatsworth, Calif.) according to the manufacturer's instructions. The purified PCR product was subsequently cloned into a pCRII vector (Invitrogen, San Diego, Calif.) and the DNA sequence was determined using lac forward and reverse primers (New England BioLabs, Beverly, Mass.).

The aminopeptidase II gene segment (309 bp) consisting of 103 codons was amplified from *Aspergillus oryzae* 1568 with the aminopeptidase II-specific PCR primers described above. DNA sequence analysis showed that the amplified gene segment encoded a portion of the corresponding *Aspergillus oryzae* 1568 aminopeptidase II gene. The aminopeptidase II gene segment was used to probe the *Aspergillus oryzae* 1568 cDNA library described in Example 5.

Example 7

Identification of *Aspergillus oryzae* 1568 Aminopeptidase II Clones

The *Aspergillus oryzae* 1568 cDNA library was plated on Luria plus 50 μg/ml carbenicillin agar plates. Colony lifts (Maniatis et al., 1982, *Molecular Cloning, A Laboratory Manual*, Cold Spring Harbor Press, Cold Spring Harbor, N.Y.) were performed on approximately 10,000 colonies and the DNA was cross-linked onto membranes (Hybond N+, Amersham, Arlington Heights, Ill.) using a UV Stratalinker (Stratagene, La Jolla, Calif.). The membranes were soaked for three hours at 45° C. in a hybridization solution containing 5×SSPE, 0.3% SDS, 50% formamide, and 10 μg/ml of denatured and sheared herring sperm DNA. The aminopeptidase II gene fragment isolated from the *Aspergillus oryzae* 1568 as described in Example 6 was radiolabeled using the Random Primed DNA Labeling Kit (Boehringer Mannheim, Mannheim, Germany), denatured by adding NaOH to a final concentration of 0.1M, and added to the hybridization solution at an activity of approximately $1 \times 10^6$ cpm per ml of hybridization solution. The mixture was incubated overnight at 45° C. in a shaking water bath. Following incubation, the membranes were washed three times in 2xSSC with 0.2% SDS at 55° C. The membranes were then dried on blotting paper for 15 minutes, wrapped in SaranWrap™, and exposed to X-ray film for 48 hours at −70° C. with intensifying screens (Kodak, Rochester, N.Y.).

Eleven colonies produced strong hybridization signals with the probe. The eleven colonies were inoculated into five ml of LB plus 50 μg/ml carbenicillin medium and grown overnight at 37° C. Miniprep DNA was prepared from each of these clones using the Wizard 373 DNA Purification Kit (Promega, Madison, Wis.). Clone 9 and clone 10 contained aminopeptidase II encoding sequence, as confirmed by DNA sequencing. Clone 9 (pEJG18) was full length. The plasmid pEJG18 was subcloned in *E. coli* DH5α cells to produce *E. coli* DH5αEJG18.

Example 8

DNA sequence analysis of *Aspergillus oryzae* 1568 Aminopeptidase II Gene

DNA sequencing of the aminopeptidase II gene contained in pEJG18 in *E. coli* DH5αEJG18 described in Example 7 was performed with an Applied Biosystems Model 373A Automated DNA Sequencer (Applied Biosystems, Inc., Foster City, Calif.) on both strands using the primer walking technique with dye-terminator chemistry (Giesecke et al., 1992, *Journal of Virology Methods* 38: 47–60). Oligonucleotide sequencing primers were designed to complementary sequences in the aminopeptidase II gene and were synthesized on an Applied Biosystems Model 394 DNA/RNA Synthesizer according to the manufacturer's instructions.

The nucleotide sequence of the gene encoding the *Aspergillus oryzae* 1568 aminopeptidase II and the deduced amino acid sequence thereof is shown in FIG. 1 (SEQ ID NOS:1 and 2, respectively). Sequence analysis of the cloned insert revealed a large open reading frame of 1488 nucleotides (excluding the stop codon) encoding a protein of 496 amino acids sequence (SEQ ID NO:2). The G+C content of this open reading frame is 58%. Based on the rules of van Heijne (van Heijne, 1984, *Journal of Molecular Biology* 173: 243–251), the first 15 amino acids likely comprise a secretory signal peptide which directs the nascent polypeptide into the endoplasmic reticulum (double underlined in FIG. 1).

The amino acid sequences of the partial peptides derived from the purified aminopeptidase II as described in Example 2 are underlined in FIG. 1 and were consistent with those found in the deduced amino acid sequence (SEQ ID NO:2) of the *Aspergillus oryzae* 1568 aminopeptidase II cDNA.

Using the Clustal alignment program (Higgins, 1989, supra) to compare the deduced amino acid sequence of the *Aspergillus oryzae* 1568 aminopeptidase II to that of the Saccharmyces cerevisiae aminopeptidase II Y (SEQ ID NO:5), a 33.7% identity was observed.

Example 9

Construction of an *Aspergillus oryzae* 1568 Aminopeptidase II Expression Vector for an Aspergillus Host Two synthetic oligonucleotide primers shown below were designed to PCR amplify the *Aspergillus oryzae* A1568 aminopeptidase II gene coding sequence from plasmid pEJG18 (*E. coli* DH5α-EJG18) for subcloning and expression in an Aspergillus host.

Forward primer: 5'-ATGATGAGGTCGCTTTT-GTGGGC-3' (SEQ ID NO:6)

Reverse primer: 5'-GGGATGCATCTATGCCTCGACTT-3' (SEQ ID NO:7)

Bold letters represent coding sequence.

In order to facilitate the subcloning of the gene fragment into an expression vector designated pMWR3 (FIG. 2), a NsiI restriction enzyme site was introduced at the 3' end of the aminopeptidase II gene. The 5' end was left blunt with an addition of ATG for insertion into the SwaI site. The vector pMWR3 contained the TAKA promoter and terminator as regulatory sequences. Since the plasmid does not contain a selectable marker for fungal transformations, it was cotransformed with pToC90 (WO 91/17243) which contains amdS as the selectable marker.

Figure 3:
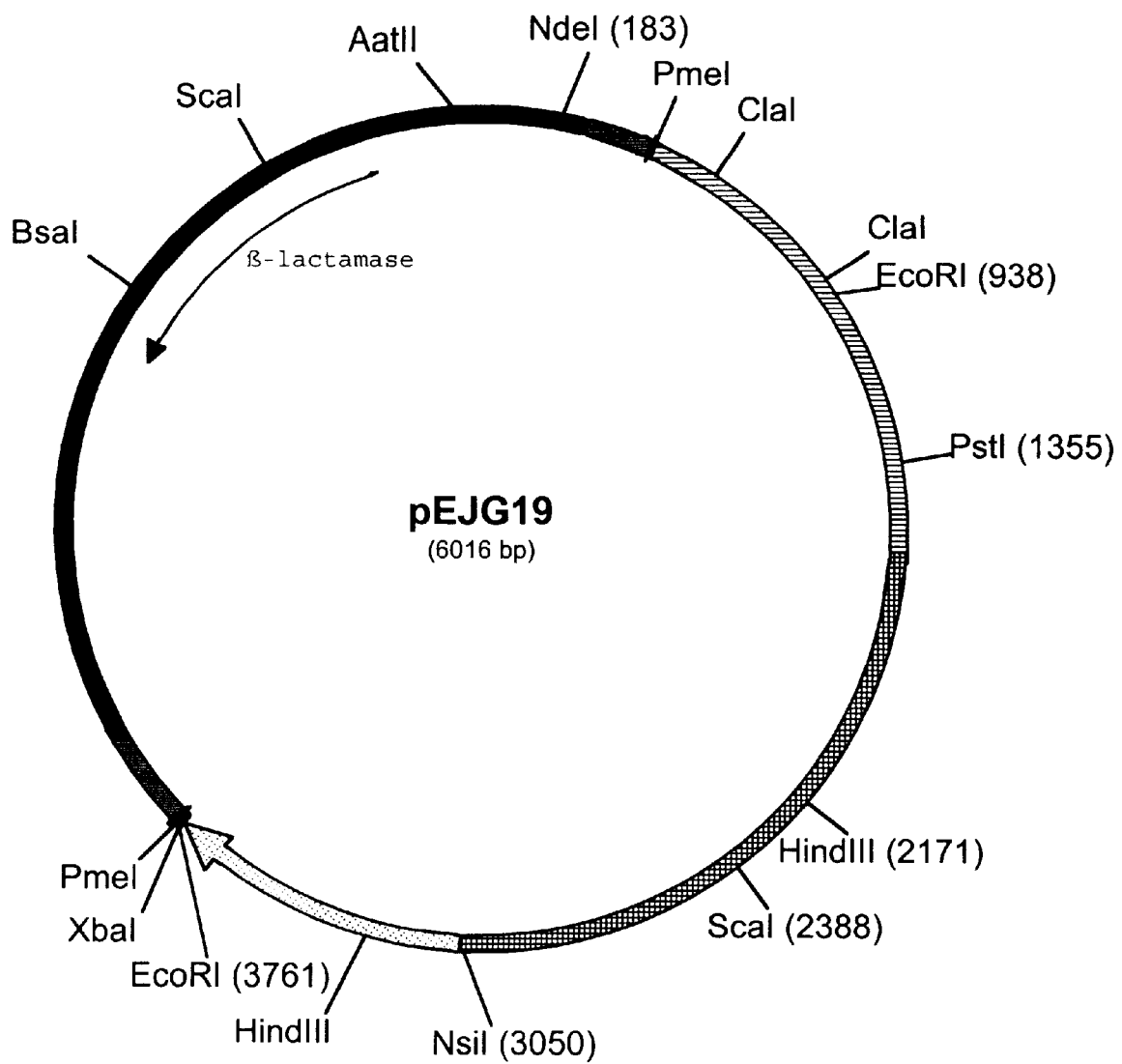
FIG. 3 shows a restriction map of pEJG19.

Fifty picomoles of each of the primers above were used in a PCR reaction (50 1) containing 70 ng of pEJG18 (an *Aspergillus oryzae* 1568 cDNA clone in pYES2), 1X Pwo Buffer (Boehringer Mannheim, Indianapolis, Ind.), 8 μl of a 10 mM blend of dATP, dTTP, dGTP, and dCTP, and 2.5 units of PwoI (Boehringer Mannheim, Indianapolis, Ind.). The amplification conditions were one cycle at 94° C. for 2 minutes, 55° C. for 30 seconds, and 72° C. for 1 minute; 9 cycles at 94° C. for 15 seconds, 55° C. for 30 seconds, and 72° C. for 1 minutes; 15 cycles at 94° C. for 15 seconds, 55° C. for 30 seconds, and 72° C. for 1 minute, with an extension of 20 seconds per cycle; and a final cycle of 94° C. for 15 seconds, 55° C. for 30 seconds, and 72° C. for 7 minutes. The heat block then went to a 4° C. soak cycle. The amplified 1500 bp DNA fragment was purified by gel electrophoresis and Qiaex II. The aminopeptidase clone was digested with NsiI (using conditions specified by the manufacturer). The fragment was phenol-chloroform extracted and ethanol precipitated. The cut fragment was cloned into pMWR3 that had been previously cut with SwaI and NsiI resulting in the expression plasmid pEJG19 (FIG. 3) in which transcription of the aminopeptidase II gene was under the control of the TAKA promoter. The plasmid pEJG19 was transformed into *E. coli* DH5α cells (Life Technologies, Gaithersburg, Md.). An *E. coli* transformant containing the pEJG19 plasmid was isolated and plasmid DNA was prepared according to procedures described by Sambrook et al., 1989, supra.

Example 10

Expression of the *Aspergillus oryzae* 1568 Aminopeptidase II Gene in *Aspergillus oryzae*

Plasmid pEJG19 was introduced into an alkaline protease-deficient *Aspergillus oryzae* host JaL142-6 using the following protoplast transformation methods. The transformation was conducted with protoplasts at a concentration of ca. $2 \times 10^7$ protoplasts per ml. One hundred μl of protoplasts were placed on ice with ca. 5 μg of pEJG19 and 5 μg of pTOC90; 250 μl of 60% PEG 4000, 10 mM Tris-HCl, pH 7.5, 10 mM $CaCl_2$ was added, and the protoplasts were incubated at 37° C. for 30 minutes. Three mls of STC (1.2 M Sorbitol, 10 mM Tris-HCl, pH 7.5, and 10 mM $CaCl_2$) was added. The solution was mixed gently and poured onto COVE transformation plates (per liter: 0.52 g of KCl, 0.52 g of $MgSO_4$-$7H_2O$, 1.52 g of $KH_2PO_4$, 1 ml of trace metals described below, 342.3 g of sucrose, 25 g of Noble agar, 10 ml of 1 M acetamide, 10 ml of 3 M CsCl). The trace metals solution (1000x) was comprised of 22 g of $ZnSO_4$-$7H_2O$, 11 g of H$_3$BO$_3$, 5 g of MnCl$_2$-4H$_2$O, 5 g of FeSO$_4$-7H$_2$O, 1.6 g of CoCl$_2$-5H$_2$O, 1.6 g of (NH$_4$)$_6$Mo$_7$O$_{24}$, and 50 g of Na$_4$EDTA per liter. Plates were incubated 7 days at 37° C. Transformants were transferred to plates of the same medium and incubated 2 days at 37° C. Totally, 140 transformants were recovered by their ability to grow on COVE medium using acetamide as sole nitrogen source.

The transformants were grown for 4 days at 34° C., 200 rpm in 24 well plates containing 1 ml per well of 25% MY50 medium diluted with 75% MY50 salts. MY50 was composed per liter of 50 g of maltodextrin, 2.0 g of MgSO$_4$-7H$_2$O, 10 g of KH$_2$PO$_4$, 2 g of citric acid, 10 g of yeast extract, 2.0 g of urea, 2 g of K$_2$SO$_4$ and 0.5 ml of trace elements solution adjusted to pH 6.0. The trace metals solution was compsoed per liter of 14.3 g of is ZnSO$_4$-7H$_2$O, 2.5g of CuSO$_4$-5H$_2$O, 0.5g of NiCl$_2$-6H$_2$O, 13.8 g of FeSO$_4$-7H$_2$O, 8.5 g of MnSO$_4$-H$_2$O, 3 g of citric acid. The MY50 salts was composed per liter of 2.0 g of MgSO$_4$-7H$_2$O, 10 g of KH$_2$PO$_4$, 2 g of citric acid, and 2 g of K$_2$SO$_4$, pH 6.0.

Each of the 140 wells were assayed for aminopeptidase II activity using Leu-pNA (hydrochloride salt) as substrate. In a 96 well microtiter plate, 4 μl of supernatant was added to 100 μl of 1 mg/ml of Leu-pNA in 50 mM sodium phosphate pH 7.5 buffer. The absorbance at 405 nm was monitored.

Four transformants, 20, 88, 90, and 137, with the highest level of aminopeptidase II activity were then grown in 125 ml shake flasks for 4 days at 34° C. containing 25 ml of MY50 medium.

Samples were assayed on day 2, 3, and 4 for aminopeptidase II activity by mixing 100 μl of 10-fold diluted supernatant with 100 μl of 2 mg/ml Leu-pNA in 50 mM sodium phosphate pH 7.5 buffer. Transformants 20, 90, and 137 were the highest producers. for For purification of the aminopeptidase II, transformants 20 and/or 90 were grown in shake flasks as above or in a fermentation medium composed of suitable carbon and nitrogen sources.

Example 11

Purification of Recombinant *Aspergillus oryzae* 1568 Aminopeptidase II Produced in Aspergillus The combined supernatants from the shake flask broths described in Example 10 were combined (approximately 100 mg of protein in approximately 100 ml) and was diluted to 3.7 mS and adjusted to pH 7.0. The diluted sample was then loaded onto Q-Sepharose, Big Beads, pre-equilibrated with 20 mM sodium phosphate pH 7.0 buffer. The aminopeptidase II was eluted with a 0–0.4 M NaCl gradient in 20 mM sodium phosphate pH 7.0 buffer followed by a wash with 0.4 M NaCl. Fractions were assayed for aminopeptidase II activity by mixing 100 μl of each fraction with 100 μl of 2 mg of Leu-pNA per ml of 50 mM sodium phosphate pH 7.5 buffer. The assay results indicated that the aminoepeptidase II eluted at the end of the gradient and during the 0.4 M NaCl wash. Analysis by SDS-PAGE revealed that the enzyme was homogeneous.

Example 12

Construction of an *Aspergillus oryzae* 1568 Aminopeptidase II Expression Vector for a Fusarium Host Two synthetic oligonucleotide primers shown below were designed to PCR amplify the *Aspergillus oryzae* A1568 aminopeptidase II gene coding sequence from plasmid pEJG18 (*E. coli* DH5α-EJG18) for subcloning and expression in a Fusarium host.

Forward primer: 5'-ATTTAAATcaccATGAGGTC-GCTTTTGTGGGC-3' (SEQ ID NO:8)

Reverse primer: 5'-GGGTTAATTAACTATGCCT-CGACTTGAGAATG-3' (SEQ ID NO:9)

Bold letters represent coding sequence. Small case represents a Kozak consensus sequence to enhance expression (Kozak, 1981, Nucleic Acids Research 12. 857–872).

Figure 4:
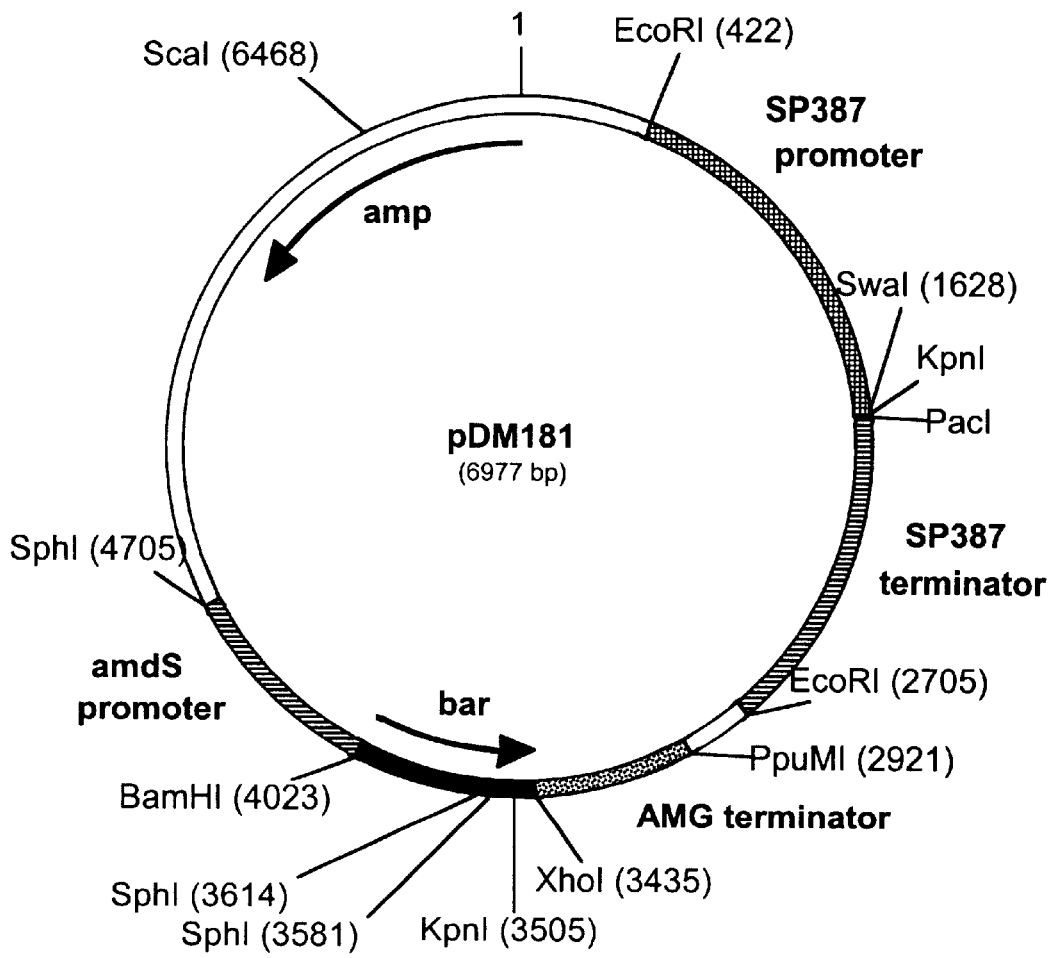
FIG. 4 shows a restriction map of pDM181.

In order to facilitate the subcloning of the gene fragment into an expression vector designated pDM181 (FIG. 4), SwaI and PacI restriction enzyme sites were introduced at the 5' and 3' end of the aminopeptidase II gene, respectively. The vector pDM181 contained the *Fusarium oxysporum* trypsin-like protease (SP387) promoter and terminator (WO 96/00787) as regulatory sequences. The plasmid also contained the bar gene as a selectable marker for fungal transformations (de Block et al., 1987, *EMBO Journal* 6:2513–2518).

Figure 5:
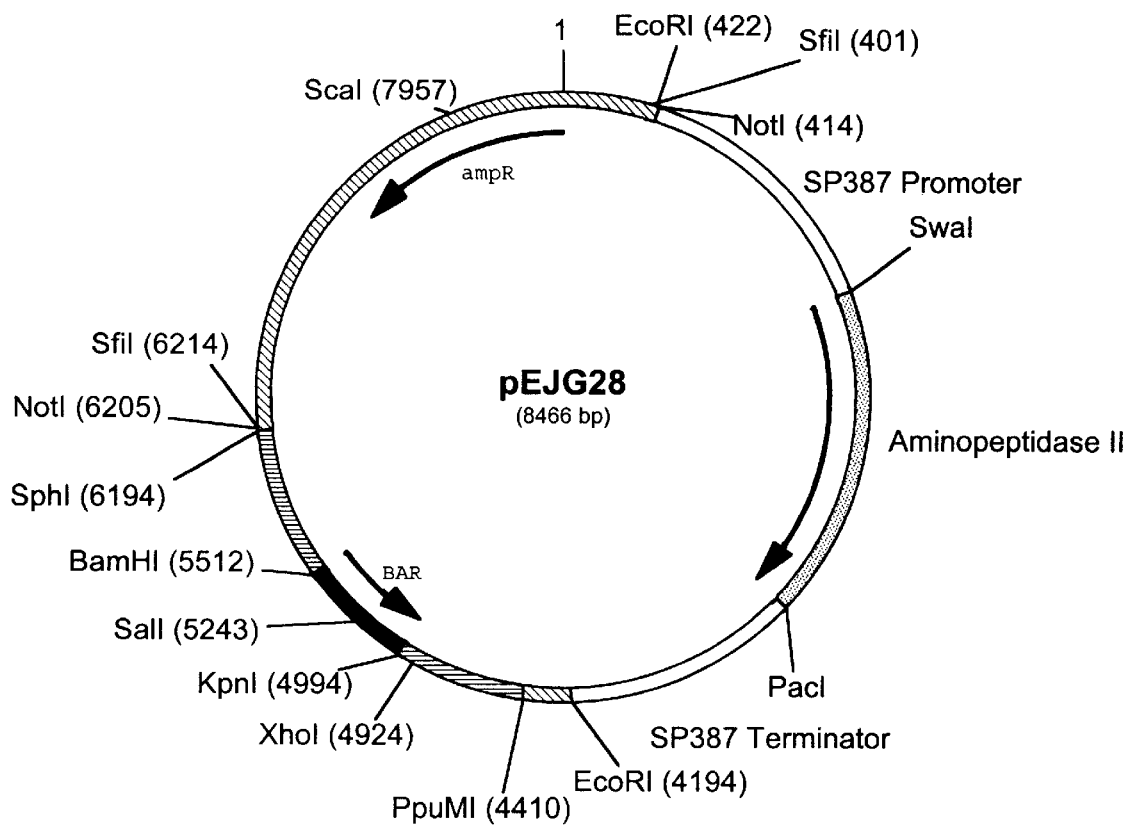
FIG. 5 shows a restriction map of pEJG28.

Fifty picomoles of each of the primers above were used in a PCR reaction containing 70 ng of pEJG18, 1×Pwo Buffer, 5 μl of 10 mM blend of dATP, dTTP, dGTP, and dCTP, and 2.5 units of PwoI. The amplification conditions were one cycle at 94° C. for 2 minutes, 55° C. for 30 seconds, and 72° C. for 1 minute; 9 cycles each at 94° C. for seconds, 55° C. for 30 seconds, and 72° C. for 1 minute; 15 cycles each at 94° C. for 15 seconds, 55° C. for 30 seconds, and 72° C. for 1 minute, with an extension of 20 seconds per cycle; and a final cycle at 94° C. for 15 seconds, 55° C. for 30 seconds, and 72° C. for 7 minutes. The heat block was then held at a 4° C. soak cycle. The amplified 1500 bp DNA fragment was purified by gel electrophoresis and Qiaex II, and then subcloned into pCRII TOPO TA cloning vector (Stratagene, San Diego, Calif.). The pCRII aminopeptidase clone was cut with restriction endonucleases SwaI and PacI (using conditions specified by the manufacturer). The fragment was purified by gel electrophoresis and Qiaex II. The cut fragment was cloned into pDM181 that had been previously cut with SwaI and PacI resulting in the expression plasmid pEJG28 (FIG. 5) in which transcription of the aminopeptidase II gene was under the control of the *Fusarium oxysporum* trypsin-like protease promoter. The plasmid pEJG28 was transformed into *E. coli* ABLE K cells (Stratagene, San Diego, Calif.). The *E. coli* transformant containing the pEJG28 plasmid was isolated and plasmid DNA was prepared according to procedures described by Sambrook et al., 1989, supra.

Example 13

Transformation of Fusarium CC1-3 and Analysis of Transformants

Fusarium strain CC1-3, a highly branched morphological mutant of Fusarium strain A3/5 (ATCC 20334) (Wiebe et al., 1992, *Mycological Research* 96: 555–562; Wiebe et al., 1991, *Mycological Research* 95: 1284–1288; Wiebe et al., 1991, *Mycological Research* 96: 555–562), was grown in a liquid medium containing Vogel's salts (Vogel, 1964, *Am. Nature* 98: 435–446), 25 mM NaNO$_3$, and 1.5% glucose for 4 days at 28° C. and 150 rpm. Conidia were purified by filtration through 4 layers of cheesecloth and finally through one layer of Miracloth. Conidial suspensions were concentrated by centrifugation. Fifty ml of YPG medium comprised of 1% yeast extract, 2% bactopeptone, and 2% glucose were inoculated with approximately 10$^8$ conidia, and incubated for 14 hours at 24° C. and 150 rpm. Resulting hyphae were trapped on a sterile 0.4 mm filter and washed successively with sterile distilled water and 1.0 M $MgSO_4$. The hyphae were resuspended in 10 ml of NOVOZYM 234™ solution (2–10 mg/ml in 1.0 M $MgSO_4$) and digested for 15–30 minutes at 34° C. with agitation at 80 rpm. NOVOZYM 234™ was obtained from Novo Nordisk A/S, Bagsvaerd, Denmark. Undigested hyphal material was removed from the resulting protoplast suspension by successive filtration through 4 layers of cheesecloth and through Miracloth. Twenty ml of 1 M sorbitol were combined with the protoplast solution. After mixing, the protoplasts were pelleted by centrifugation and washed successively by resuspension and centrifugation in 20 ml of 1 M sorbitol and in 20 ml of STC (0.8 M sorbitol, 0.05 M Tris pH 8.0, 0.05 M $CaCl_2$). The washed protoplasts were resuspended in 4 parts STC and 1 part SPTC (0.8 M sorbitol, 40% PEG 4000, 0.05 M Tris pH 8.0, 0.05 M $CaCl_2$) at a concentration of 5×10'/ml.

One hundred ml of protoplast suspension were added to 10 µg of pEJG28 in polypropylene tubes (17×100 mm), mixed and incubated on ice for 30 minutes. One ml of SPTC was mixed gently into the protoplast suspension and incubation was continued at room temperature for 20 minutes. 12.5 ml of molten solution (cooled to 40° C.) consisting of 1×Vogel's salts, 25 mM $NaNO_3$, 0.8 M sucrose and 1% low melting agarose (Sigma Chemical Company, St. Louis, Mo.) were mixed with the protoplasts and then plated onto an empty 100 mm Petri plate. Incubation was continued at room temperature for 10 to 14 days. After incubation at room temperature for 24 hours, 12.5 ml of the identical medium plus 10 mg of BASTA™ (Hoechst Schering, Rodovre, Denmark) per ml were overlayed onto the Petri plate. BASTA™ was extracted twice with phenol:chloroform:isoamyl alcohol (25:24:1), and once with chloroform:isoamyl alcohol (24:1) before use.

After two weeks, 2 transformants designated #1 and #2 were apparent. A mycelial fragment from the edge of each transformant was transferred to individual wells of a 24 well plate containing Vogel's/ BASTA™ medium. The medium contained 25 g of sucrose, 25 g of Noble agar, 20 ml of 5×Vogel's salts (Vogel, 1964, supra), 25 mM $NaNO_3$, and 10 g of BASTA™ per liter. The plate was sealed in a plastic bag to maintain moisture and incubated approximately one week at room temperature.

Example 14

Expression of *Aspergillus oryzae* 1568 Aminopeptidase II Gene in Fusarium

A mycelial fragment from each of the 2 Fusarium CC1-3 transformants described in Example 13 was inoculated into 20 ml of M400Da medium composed of 50 g of maltodextrin, 2.0 g of $MgSO_4$-$7H_2O$, 2.0 g of $KH_2PO_4$, 4.0 g of citric acid, 8.0 g of yeast extract, 2.0 g of urea, and 0.5 ml of trace metals solution per liter and incubated for 7 days at 30° C. and 150 rpm. The medium was adjusted to pH 6.0 with 5 N NaOH. The trace metals solution contained 14.3 g of $ZnSO_4$-$7H_2O$, 2.5 g of $CuSO_4$-$5H_2O$, 0.5 g of $NiCl_2$-$6H_2O$, 13.8 g of $FeSO_4$-$7H_2O$, 8.5 g of $MnSO_4$-$H_2O$, and 3.0 g of citric acid per lite untransformed host was also run as a control. One ml of culture supernatant was harvested at 7 days and stored and assayed. Aminopeptidase II activity was determined by mixing 10 µl of supernatant with 200 µl of a substrate stock solution containing 2 mg of Leu-paranitroanilide per ml of 50 mM sodium phosphate pH 7.5 buffer and monitoring the change in absorbance at 405 nm over 4 minutes. Both transformants exhibited activity towards Leu-pNA greater than the untransformed control.

The primary Fusarium transformant #2 described in Example 13 was cultivated in 125 ml shake flasks for 5 days at 30° C. in 25 ml of M400Da medium. The whole culture broth was filtered using a double layer of Miracloth. The filtrate was recovered and then frozen at −20° C.

Example 15

Purification of Recombinant *Aspergillus oryzae* 1568 Aminopeptidase II Produced by Fusarium A 20 ml volume of a 5 day Fusarium broth described in Example 14 was filtered through a 0.45 micron syringe filter. The sample was then diluted 8-fold in 20 mM sodium phosphate buffer pH 7.0 buffer. The conductivity and pH of the sample was 3.1 mS and 7.10, respectively. The sample was loaded onto a XK-26 (Pharmacia Biotech AB, Uppsala, Sweden) column containing 60 ml of Q-Sepharose, Big Beads, which had been pre-equilibrated with 20 mM sodium phosphate pH 7.0 buffer. The column was washed until a baseline was reached and then the sample was eluted with a linear gradient from 0–0.5 M NaCl in 20 mM sodium phosphate buffer pH 7.0 over 8.3 column volumes and at a flow rate of 5 ml/min. Fractions were assayed using Leu-pNA as substrate by mixing 10 µl of each fraction with 90 µl of 50 mM sodium phosphate pH 7.5 buffer and 100 µl of a substrate stock solution containing 2 mg of Leu-pNA per ml of 50 mM sodium phosphate pH 7.5 buffer and monitoring the change in absorbance at 405 nm over 4 minutes. All fractions active on Leu-pNA were then pooled, diluted, and concentrated using an Amicon Ultrafiltration unit utilizing a PM 10 membrane.

The concentrated sample was then loaded onto a Mono Q 16/10 (Pharmacia Biotech AB, Uppsala, Sweden) column which had been pre-equilibrated with 20 mM sodium phosphate pH 7.0 buffer. The column was then washed with 0.15 M NaCl. A gradient was performed from 0.15–0.5 M NaCl over 10 column volumes at a flow rate of 2 µl/min. Active fractions were then equilibrated in 1.7 M $(NH_4)_2SO_4$ in 50 mM sodium phosphate buffer pH 7.0.

The sample was then loaded onto a Phenyl Superose 5/5 column (Pharmacia Biotech AB, Uppsala, Sweden) which had been pre-equilibrated with 1.7 M $(NH_4)_2SO_4$ in 50 mM sodium phosphate pH 7.0 buffer. The column was washed with 1.7 M $(NH_4)_2SO_4$ in 50 mM sodium phosphate pH 7.0 buffer until baseline was achieved. The enzyme was eluted with a gradient from 1.7 M to 0 M $(NH_4)_2SO_4$ over 30 column volumes at a flow rate of 0.5 ml/min. The flow through had activity on Leu-pNA, as did fractions that were eluted. The enzyme appeared as a series of differentially glycosylated forms based on SDS-PAGE analysis. When the various forms of the enzyme were treated with Endoglycosidase F/N glycosidase F (Boehringer Mannheim, Indianapolis, Ind.), according to the manufacturer's suggested protocol, a single band with a molecular weight of ~58 kDa appeared in all the samples analyzed. The differentially glycosylated forms were then pooled, desalted using 50 mM sodium phosphate buffer pH 7.5, and submitted to biochemical characterization.

Example 16

Characterization of Recombinant *Aspergillus oryzae* 1568 Aminopeptidase II

The purified aminopeptidase II described in Example 11 was used in the following characterization.

Kinetic parameters of the aminopeptidase II were determined for several p-nitroanilides (pNA) including Leu-pNA, Gly-pNA, Ala-pNA, and Pro-pNA (Sigma Chemical Co., St.

Louis, Mo., or Bachem, Torrance, Calif.). Stock solutions of 100 mg of each p-nitroanilide per ml of dimethylsulfoxide were diluted with 50 mM potassium phosphate pH 7.0 buffer to concentrations ranging from 0.0064 to 9.56 mM. It should be noted that the solubility of the substrates is not always sufficient to have concentrations comparable to $K_m$, which may result in errors which could be higher than expected normally. The reaction of the aminopeptidase II with the p-nitroanilide was initiated when a 100 µl aliquot of the enzyme solution in 50 mM potassium phosphate pH 7.0 was added to 100 µl of a substrate solution in a microtiter plate well and monitored at 405 nm and 25° C. using a THERMOmax Microplate Reader (Molecular Devices Corp., Sunnyvale, Calif.). Analysis of initial rates of hydrolysis of the p-nitroanilides produced the results shown in Table 1:

TABLE 1

Kinetic parameters of aminopeptidase II at pH 7.0 and 25° C.

| Substrate | $K_m$ (mM) | $V_{max}$ (relative units) |
|---|---|---|
| Leu-pNA | 7 | 6400 |
| Gly-pNA | 0.3 | 1670 |
| Ala-pNA | 11 | 1200 |
| Pro-pNA | 2 | 120 |

The results showed that the aminopeptidase II possesses a substrate specificity where the specificity toward Ala is much worse than toward Gly.

Inhibition of the aminopeptidase II with 1,10-phenanthroline was evaluated using Leu-pNA as substrate at pH 7.5 in 50 mM Tris pH 7.5 buffer where hydrolysis was monitored at 405 nm. A 200 mM solution of 1,10-phenanthroline in methanol was prepared. The inhibition reaction was conducted by mixing 100 µl of 2 mg of Leu-pNA per ml of 50 mM sodium phosphate pH 7.5 solution and 10 µl of the 1,10-phenanthroline solution with 100 µl of aminopeptidase II diluted 5-fold in 50 mM sodium phosphate pH 7.5 buffer. A control was run where 10 µl of 20 mM Tris pH 7.6 buffer was used in place of the 1,10-phenantholine solution.

The results indicated that 1, 10-phenanthroline inhibited the aminopeptidase II suggesting that the aminopeptidase II is a metalloprotease. The rate of hydrolysis of Leu-pNA decreased from 285 mOD/minute to 21 mOD/minute in the presence of 1,10-phenanthroline.

The purified aminopeptidase II described in Example 15 was used in the following characterizations.

The pH optimum was determined using Ala-pNA as substrate in the universal buffer composed of 0.125 M citric acid, 0.125 M mono basic sodium phosphate, and 0.125 M boric acid pH was adjusted to 4.5–11 with 10 N NaOH, in 0.5 pH increments. The Ala-pNA substrate was prepared by dissolving 100 mg of Ala-pNA in 1 ml of DMSO and adding 20 µl of the Ala-pNA/DMSO solution to 980 µl of the universal buffer at the various pH values. The assay was initiated by adding a 15 µl aliquot of the aminopeptidase II in 50 mM sodium phosphate pH 7.5 buffer to 200 µl of 2 mg/ml Ala-pNA at the various pH values at ambient temperature. The change in absorbance at 405 nm was monitored for 5 minutes. Autohydrolysis of the substrate as a control was determined by adding 15 µl of 50 mM sodium phosphate pH 7.5 buffer to 200 µl of 2 mg/ml Ala-pNA at the various pH values.

The results shown in Table 2 below demonstrated that the aminopeptidase II possessed activity with Ala-pNA as substrate over the measured pH range 4.91 to 10.91 with optimal activity at pH ~9.5–10. No autohydrolysis of the substrate was observed at pH values of 11 or less.

TABLE 2

| pH | Avg. Activity | Relative Activity |
|---|---|---|
| 4.42 | 0 mOD/min | 0 |
| 4.91 | 2 | 0.006 |
| 5.41 | 7.8 | 0.024 |
| 5.89 | 13.9 | 0.043 |
| 6.40 | 16.37 | 0.051 |
| 6.90 | 23.48 | 0.0727 |
| 7.27 | 41.24 | 0.128 |
| 7.59 | 69.15 | 0.214 |
| 8.03 | 145.6 | 0.45 |
| 8.62 | 245.99 | 0.761 |
| 9.25 | 306.97 | 0.95 |
| 9.68 | 323.15 | 1.0 |
| 10.51 | 270.8 | 0.838 |
| 10.95 | 197.86 | 0.612 |

The temperature stability of the aminopeptidase II was determined using the following protocol: 480 µl of 50 mM sodium phosphate buffer pH 7.5 was preincubated at 37°, 45°, 55°, 60°, 65°, 70°, and 75° C. for 30 minutes in a 1.7 ml Eppendorf tube. Then 20 µl of purified aminopeptidase II was added and the sample was then incubated for an additional 20 minutes. The samples were then placed on ice. Once the incubations were completed for all the temperatures, the samples were then assayed for activity using Leu-pNA as substrate.

The assay was performed by mixing 100 µl of the incubation mixtures for the various temperatures with 100 µl of 2 mg/ml Leu-pNA in 50 mM sodium phosphate pH 7.5 buffer at ambient temperature. The absorbance at 405 nm was monitored for 5 minutes.

The results shown in Table 3 demonstrated that the aminopeptidase II retained 90% of its activity after a 20 minute incubation at 60° C., pH 7.5.

TABLE 3

| Temperature (° C.) | Percent activity relative to 37° C. |
|---|---|
| 37 | 100 |
| 45 | 101 |
| 55 | 99 |
| 60 | 90 |
| 65 | 73.7 |
| 70 | 64.6 |
| 75 | 46 |

The kinetic parameters for various aminopeptidase II substrates was determined using the following protocol. Purified aminopeptidase II with an $A_{280}$ of 0.581 was used. Each substrate was dissolved in DMSO to a concentration of 100 mg/ml and then diluted 50 fold in 50 mM sodium phosphate pH 7.5 buffer to 2 mg/ml. The substrates included Leu-pNA, Glu-pNA (Bachem, Torrance, Calif.), and Ala-pNA. In a 96 well microtiter plate, 10 µl of purified aminopeptidase II was incubated with each substrate as follows except 50 µl of purified aminopeptidase II was incubated with Glu-pNA, and the absorbance at 405 nm was measured for 4 minutes:

1. 200 µl of 2 mg/ml substrate +0 µl of 50 mM sodium phosphate buffer pH 7.5
2. 100 µl of 2 mg/ml substrate +100 µl of 50 mM sodium phosphate buffer pH 7.5
3. 50 µl of 2 mg/ml substrate +150 µl of 50 mM sodium phosphate buffer pH 7.5

4. 25 µl of 2 mg/ml substrate +175 µl of 50 mM sodium phosphate buffer pH 7.5

A Lineweaver-Burke plot was constructed to determine the $K_m$ and the $k_{cat}$ for each substrate, using an average molecular weight of 97 kDa for the differentially glycosylated forms.

For Leu-pNA, the $K_m$ and $k_{cat}$ were determined to be 5.78 mM and 230.9 mim$^{-1}$, respectively.

For Glu-pNA, the $K_m$ and $k_{cat}$ were determined to be 1.17 mM and 8.217 mim$^{-1}$, respectively.

For Ala-pNA, the $K_m$ and $k_{cat}$ were determined to be 1.49 mM and 34.638 mim$^{-1}$, respectively.

Example 17

Preparation of Protein Hydrolysates with *Aspergillus oryzae* 1568 Aminopeptidase II The purified aminopeptidase II described in Example 11 was tested in degree of hydrolysis assays using soy, wheat gluten, and casein as substrates according to the following procedure.

The degree of hydrolysis (DH) assays were performed at 50° C. for 18 hours as a mini-hydrolysis on a 10 ml scale using soy bean meal tablets, wheat gluten meal tablets, and sodium-caseinate at a 2% concentration adjusted to pH 7, if necessary, with no pH adjustment during hydrolysis. The hydrolysates were inactivated at 85° C. for 3 minutes in a waterbath. The enzymes used were FLAVOURZYME™ and aminopeptidase II. The enzymes were dosed as follows. For soy, 2 LAPUs and 5 LAPUs of aminopeptidase II (recombinant) were added compared to 3 LAPUs of FLAVOURZYME™. For gluten, 2 LAPUs and 5 LAPUs of aminopeptidase II (recombinant) were added compared to 3 LAPUs of FLAVOURZYME™. For casein, 1 and 2 LAPUs of aminopeptidase II (recombinant) were added compared to 3 LAPUs of FLAVOURZYME™. One LAPU (Leucine Amino Peptidase Unit) is the amount of enzyme which decomposes 1 micromole of L-leucine-p-nitroanilide per minute under the following conditions: 26 mM L-leucine-p-nitroanilide in 0.1 M Tris pH 8.0 buffer at 40° C. for 10 minutes. Upon hydrolysis, p-nitroanilide is liberated turning the solution yellow which is monitored 405 nm.

The degree of hydrolysis (DH), as defined as described by Adler-Nissen (1986, *Enzymic Hydrolysis of Food Proteins*, Elsevier Applied Science Publishers), was determined by reaction of the supernatant with OPA (ortho-phtaldialdehyde, Sigma Chemical Co., St. Louis, Mo.) according to the following procedure. The hydrolysate was diluted 100-fold into distilled water. Then 120 µl was transferred to 900 µl of OPA reagent. For the OPA reagent, 160 mg of OPA was dissolved in 4 ml of ethanol and transferred to a 200 ml volumetric flask containing a solution of 7.62 g of disodium tetraborate decahydrate, 200 mg of sodium dodecylsulphate, and 176 mg of dithiothreitol and the flask was filled to 200 ml with water. The solution was then shaken well and after 2 minutes exactly, the absorbance at 340 nm was measured and compared to the absorbance of a 0.95 mM L-serine (distilled water) solution after subtraction of the blank value (water reacted with OPA reagent). To determine the true DH, the serine equivalents measured in the hydrolysates were corrected with the factors suggested by Adler-Nissen for the trinitrobenzenesulfonic acid method (Adler-Nissen, 1979, *Agricultural and Food Chemistry* 17: 1256) which gave the same response as the described OPA method. The DH was calculated on the basis of the total amount of protein in the hydrolysis mixture (not on the basis of soluble protein).

A volume of 25 µl of suitably diluted supernatant was mixed with 200 µl of OPA reagent in a microtiter plate well and allowed to react for exactly 2 minutes at 25° C. The absorbance at 340 nm was measured in a microtiter plate reader and compared to the absorbance of a 95 mM L-serine standard solution after subtraction of the blank value (water reacted with OPA-reagent). To determine the true DH, the serine equivalents measured in the supernatants were corrected with the factors suggested by Adler-Nissen for the trinitrobenzenesulfonic acid method (Adler-Nissen, 1979, *Agricultural and Food Chemistry* 17: 1256) which gave the same response as the described OPA method. The degree of hydrolysis was calculated on basis of the total amount of protein in the hydrolysis mixture (not on basis of soluble protein).

For soy, the addition of 2 LAPUs and 5 LAPUs of aminopeptidase II to 3 LAPUs of FLAVOURZYME™ increased absolute DH at least 8% and 10%, respectively, above the samples with 3 LAPUs of FLAVOURZYME™ alone.

For gluten, the addition of 2 LAPUs and 5 LAPUs of aminopeptidase II to 3 LAPUs of FLAVOURZYME™ increased absolute DH 6% and 9%, respectively.

For gelatin, the addition of 2 LAPUs and 5 LAPUs of dipeptide aminopeptidase II to 3 LAPUs of FLAVOURZYME™ increased absolute DH 4.9% and 5.3% respectively.

For casein, the addition of 1 and 2 LAPUs of aminopeptidase II to 3 LAPUs of FLAVOURZYME™ increased absolute DH 7% and 9%, respectively, over the addition of 5 3 LAPUs of FLAVOURZYME™ alone.

Example 18

Hydrolysis of Soy Protein with *Aspergillus oryzae* Aminopeptidase II

Soy protein in the form of defatted soy bean meal was hydrolysed on a 10 ml-scale (mini-hydrolysis) with a start pH of 7.0 and a protein concentration of 2%. The hydrolysis time and temperature were 18 hours and 50° C., respectively. Enzymes were inactivated at 85° C. for 5 minutes and the hydrolysates were centrifuged. The supernatants were analysed for DH using the OPA-method. The DH, as defined as described by Adler-Nissen (1986, *Enzymic Hydrolysis of Food Proteins*, Elsevier Applied Science Publishers), was determined by reaction of the supernatant with OPA (ortho-phtaldialdehyde, Sigma Chemical Co., St. Louis, Mo.) according to Church et al., 1983, *Journal of Dairy Science* 66: 1219–1227. For the OPA reagent, 160 mg of OPA was dissolved in 4 ml of ethanol and transferred to a 200 ml volumetric flask containing a solution of 7.62 g of disodium tetraborate decahydrate, 200 mg of sodium dodecylsulphate, and 176 mg of dithiothreitol and the flask was filled to 200 ml with water. Selected samples were analysed for the content of free amino acids using the PicoTag HPLC method (Waters Associates, Milford, Mass.) according to the manufacturer's instructions.

The dosages of enzymes to each hydrolysis flask containing 200 mg of soy protein are shown in Table 4 below. The dosage of FLAVOURZYME™ 1000L was in percent of the soy protein substrate such that 1.5% FLAVOURZYME™ 1000L equals 3 mg of FLAVOURZYME™ 1000L added to 200 mg of soy protein. In addition to FLAVOURZYME™ 1000L, 1.5% ALCALASE® 2.4L was added to all hydrolysis flasks which equals 3 mg per 200 mg of soy protein. The aminopeptidase II was produced recombinantly in *Aspergil-*

*lus oryzae* as described in Example 10 and purified accordingly. The aminopeptidase II solution had an $A_{280}$ of 8.1 and an estimated protein content of 5 mg/ml from amino acid determination.

The results of the DH analysis are presented in Table 4. DH was calculated from total protein concentration of 2%—not the soluble protein content.

TABLE 4

The DH results for the hydrolysates

| | FLAVOURZYME ™ 1000 L (%) | Aminopeptidase II (g enzyme protein/kg soy protein)* | DH (%) |
|---|---|---|---|
| 1 | 1.5 | 0 | 45.1 |
| 2 | 1.5 | 0.03 | 50.9 |
| 3 | 1.5 | 0.06 | 51.0 |
| 4 | 1.5 | 0.12 | 51.3 |
| 5 | 1.5 | 0.25 | 55.7 |
| 6 | 1.5 | 0.50 | 58.0 |
| 7 | 2.0 | 0 | 51.9 |
| 8 | 6.0 | 0 | 62.8 |
| 9 | 6.0 | 0.03 | 62.9 |
| 10 | 6.0 | 0.06 | 62.9 |
| 11 | 6.0 | 0.12 | 63.6 |
| 12 | 6.0 | 0.25 | 68.5 |
| 13 | 6.0 | 0.50 | 67.8 |
| 14 | 7.0 | 0 | 63.2 |

*The concentration of aminopeptidase II used for this calculation is 5 mg/ml

Table 5 shows the relative % increase in the individual free amino acids upon addition of a maximal aminopeptidase II dosage (0.5 g per kg soy protein) to a background dosage of FLAVOURZYME™ and 1.5% ALCALASE® 2.4L. The increase was measured relative to the release of free amino acids resulting from the background enzyme dosages.

TABLE 5

Relative increase in free amino acids due to addition of aminopeptidase II

| Amino acid | 1.5% FLAVOURZYME ™ + Aminopeptidase II | 6% FLAVOURZYME ™ + Aminopeptidase II |
|---|---|---|
| Asp | 123.4 | 26.0 |
| Glu | 54.2 | 24.5 |
| Asn | 115.1 | −7.0 |
| Ser | 123.8 | 0.0 |
| Gln | 91.7 | 19.8 |
| Gly | 145.7 | 22.4 |
| His | 31.9 | 2.8 |
| Arg | 24.9 | 6.1 |
| Thr | 40.4 | 8.8 |
| Ala | 77.4 | 18.5 |
| Aro | 87.5 | 59.2 |
| Tyr | 51.3 | 10.5 |
| Val | 41.4 | 12.7 |
| Met | 36.8 | 9.7 |
| Cys | 74.4 | 23.2 |
| Ile | 24.6 | 13.0 |
| Leu | 22.4 | 7.5 |
| Phe | 22.8 | 8.0 |
| Lys | 49.0 | 10.3 |
| total | 49.1 | 10.6 |
| DH | 28.7 | 8.0 |

The results showed that when aminopeptidase II was added to a low dosage of FLAVOURZYME™ (1.5%) plus 1.5% ALCALASE® 2.4L, Gly showed the highest relative % increase followed by Ser, Asp, Asn, Pro, Cys, and Ala. When aminopeptidase II was added to a high FLAVOURZYME™ dosage (6%) plus 1.5% ALCALASE® 2.4L, Pro showed the highest relative % increase followed by Asp, Glu, Cys, Gly, and Gln.

Example 19

Increased Protein Solubility and Release of Glutamate by Deamidation

Wheat gluten (WG) was obtained from Cargill (JOB 5141) and deamidated wheat gluten (DWG) was obtained from StaPro Consultancy B. V., Lemdijk 32, 9422 TH Smilde, NL. Suspensions of 8% protein were made by mixing 11 g of gluten with 89 g of water. The pH was adjusted to 6.5 with NaOH. Glutamate/aspartate specific protease (SP446), obtainable as described in WO 91/13554, or lysine/arginine specific protease (SP387) obtainable as described in WO 89/06270, was added to the suspensions. The dosage was 0.01 AU/g protein for SP446 and 0.006 AU/g protein for SP387. FLAVOURZYME™ (an un-specifically acting protease preparation available from Novo Nordisk A/S, Bagsvaerd, Denmark, containing endo- and exo-peptidase activities, and obtained by fermentation of *Aspergillus oryzae*) was added to some of the hydrolysates at a dosage of 20 LAPU/g protein.

The hydrolyses were carried out at 50° C. without further pH adjustment for 18 hours. The enzymes were inactivated by heating at 85° C. for 15 minutes. The pH was adjusted to 5 and the hydrolysates were centrifuged. The content of protein and free glutamate in the supernatant was determined.

The protein content was determined by Kjeldahl analysis, using a Kjeldahl factor of 6.25.

The content of free glutamate was determined by use of a glutamate determination kit according to the manufacturer's instructions (Boehringer-Mannheim, Indianapolis, Ind.). The method was adapted for use in microtiter plates.

When comparing wheat gluten (WG) to deamidated wheat gluten (DWG), the results shown in Table 6 demonstrated that deamidation increased the susceptibility of the gluten to specific proteases, such that more protein became soluble. By addition of FLAVOURZYME™ with a specific protease, the release of glutamate was doubled due to deamidation.

TABLE 6

| | Protein Solubility - % | | Glutamate Content (mg/l) | |
|---|---|---|---|---|
| Hydrolysate | WG | DWG | WG | DWG |
| SP446 | 18 | 54 | 0 | 0 |
| SP387 | 35 | 44 | 0 | 0 |
| SP446 + FLAVOURZYME ™ | 34 | 87 | 1000 | 2000 |

Example 20

Enzymatic Deamidation and Release of Glutamate

Peptidoglutaminase II was produced by growing *Bacillus circulans* strain ATCC 21590 in shake flasks (400 ml) containing 200 ml of a medium composed of 1% polypeptone, 0.5% lactose, 0.025% $MgSO_4$-$7H_2O$, 0.005% $FeSO_4$-$7H_2O$, 0.025% $KH_2PO_4$, and 17% $Na_2HPO_4$-$12H_2O$ (pH adjusted to 7.2), at 30° C. for 20 hours with mixing at 270 rpm. The cells were harvested by centrifugation at 4000 rpm in 1 litre flasks. The cells were then frozen.

The purification of peptidoglutaminase II from *Bacillus circulans* was performed at room temperature. The frozen *Bacillus circulans* cells were thawed and suspended in Lysis buffer (50 mM Tris/HCl; 25% (w/v) sucrose; 1 mM EDTA, pH 8.0) until a homogeneous suspension was obtained—100 g wet cells per liter of Lysis buffer. Lysozyme (10 mg/ml) and DNAse I (Sigma DN-25, 10 mg/ml) were dissolved in Lysis buffer. Then 100 ml of lysozyme solution, 10 ml of 1.0 M $MgCl_2$, and 1 ml of DNAse I solution were added per litre of cell suspension. The enzymes were allowed to act for 1 hour.

The suspension was filtered through a Seitz depth filter plate and the filtrate was transferred to a 10 mM $KH_2PO_4$/NaOH, pH 8.0 (Buffer A) on a Sephadex G25 column (Pharmacia Biotech AB, Uppsala, Sweden). The enzyme solution was applied to a SOURCE Q column (Pharmacia Biotech AB, Uppsala, Sweden) equilibrated in Buffer A and eluted with a linear NaCl gradient (0→500 mM) in Buffer A. Fractions from the column were analysed for peptidoglutaminase II activity as described below and fractions with activity were pooled. The absorbance of the pooled fractions at 280 nm was 1.78, thus the protein content was estimated to 1.8 mg/ml.

The purity of the protein in the peptidoglutaminase II pool was approximately 25% as judged from a SDS-PAGE gel. Thus, the preparation contained approximately 0.5 mg/ml of pure peptidoglutaminase II.

The peptidoglutaminase activity was determined by measuring the ammonia formed during hydrolysis of γ-carboxyamide of N-tert-Butoxycarbonyl-Gln-Pro (N-t-BOC-Gln-Pro; SIGMA No. B-4403) using the Boehringer-Mannheim kit for ammonia determination (Cat. No. 1112732). In this kit, ammonia is measured by determination of the consumption of NADH by glutamate dehydrogenase, and blanks without the addition of N-t-BOC-Gln-Pro were also applied in order to subtract the effect of other NADH consuming enzymes.

A total of 200 mg of wheat gluten protein was added to 9 ml of boiling water and after cooling, the pH was adjusted to 7.0. Then 250 μl of the peptidoglutaminase II preparation (PEP) described above was added. The glutamate/aspartate specific protease (SP446) described in Example 19 was added in an amount of 0.04 AU/g protein, and FLAVOURZYME™ described in Example 19 was added in an amount of 20 LAPU/g protein.

Hydrolysis was allowed to proceed without pH adjustment for 18 hours at 50° C. Controls without the addition of peptidoglutaminase were also run. The hydrolysates were centrifuged and glutamate was measured as described in Example 19. The DH was determined as described in Example 18.

The results as shown below in Table 7 demonstrated that hydrolysis with the peptidoglutaminase preparation increased the DH as well as the release of glutamate.

TABLE 7

| Hydrolysis | DH % | Glutamate (mg/l) |
|---|---|---|
| Minus PEP | 40 | 131 |
| Plus PEP | 43 | 171 |

Example 21

Production of Crude Enzyme Extract Powder from *Spingomonas capsulata*

*Sphingomonas capsulata* IFO 12533 was cultivated at 30° C. for 9 hours with aeration and agitation in a 5 liter fermentor containing 3 liters of medium composed of 0.5% sucrose, 1% gelatin, 0.5% yeast extract, 1% corn steep liquor, 0.3% sodium chloride, 0.2% dipotassium hydrogen phosphate, and 0.1% magnesium sulfate-$7H_2O$. The cell mass was collected from the culture broth and washed twice in 10 mM Tris-HCl pH 8.0 buffer yielding 43 g wet weight of cell mass. The cell mass was suspended in 200 ml of 10 mM Tris-HCl pH 8.0 buffer and lysed by adding lysozyme and Triton X-100 at final concentrations of 1 mg/ml and 0.1%, respectively, and incubating the solution at 37° C. for one hour. The solution was ultrasonicated and then centrifuged at 15,000 g for 10 minutes. The supernatant was recovered (200 ml) and protamine sulfate was added to a final concentration of 0.1% to precipitate nucleic acids. The precipitate was discarded through centrifugation in the same fashion, and the resulting solution was used as a crude enzyme extract.

The activity of the crude enzyme extract was determined toward various synthetic peptides as shown in Table 8. The results demonstrated that the crude enzyme extract possessed dipeptidyl peptidase IV, leucine aminopeptidase, glycine aminopeptidase, and prolyl oligopeptidase activity.

TABLE 8

Activities of various peptidase activities in the crude enzyme extract solution

| Peptidase | Substrate | Activity (%) |
|---|---|---|
| prolyl oligopeptidase | Z-Ala-Ala-Pro-pNA | 46.0 |
| prolyl oligopeptidase | Z-Gly-Pro-NA | 68.7 |
| dipeptidyl peptidase IV | Gly-Pro-pNA | 21.9 |
| glycine aminopeptidase | Gly-pNA | 100 |
| leucine aminopeptidase | Leu-pNA | 67.8 |

The crude enzyme extract was precipitated by adding an equal volume of cold acetone. The enzyme precipitate was dissolved in a small volume of 10 mM phosphate pH 6.0 buffer and insoluble substances were removed by centrifugation. The enzyme was lyophilized to produce a crude enzyme powder.

Example 22

Purification of *Sphingomonas capsulata* Aminopeptidase I from Crude Enzyme Powder The crude enzyme powder described in Example 21 was dissolved in 20 mM phosphate pH 7.0 buffer and diluted until the conductivity of the sample was equivalent to the loading buffer, 20 mM phosphate pH 7.0. The sample was loaded onto a Pharmacia Q-Sepharose or Mono Q column pre-equilibrated with 20 mM phosphate pH 7.0 buffer. The flow-throughs from these columns were assayed for aminopeptidase activity with alanine-para-nitroanilide (Ala-pNA) using the procedure described below.

A stock solution of 100 mg of Ala-pNA per ml in dimethylsulfoxide was diluted with 50 mM sodium phosphate pH 7.5 buffer to a concentration of 2 mg per ml. The reaction of the aminopeptidase with the para-nitroanilide was initiated when a 10–50 μl aliquot of the enzyme solution was added to 200 μl of the substrate solution in a microtiter plate well. Analysis of initial rates of hydrolysis of the para-nitroanilide was monitored at 405 nm at room temperature in a THERMOmax Microplate Reader (Molecular Devices Corp., Sunnyvale, Calif., USA).

Aminopeptidase activity was present in the flow-through. The flow-through was concentrated using DIAFLO® PM 10 ultrafiltration membrane (Amicon, Inc., USA) and the pH of the concentrated flow-through was then adjusted to pH 6.0 using 70 mM acetate buffer pH 4.0 buffer.

The concentrated flow-through was applied to a Pharmacia Mono S 5/5 pre-packed 7×50 mm column (Pharmacia Biotech AB, Uppsala, Sweden) pre-equilibrated with 50 mM MES pH 6.0 buffer. Fractions were assayed as above for aminopeptidase activity. The bound aminopeptidase activity was eluted with a gradient from 0 to 0.2 M NaCl in 50 mM MES pH 6.0 buffer. The fractions with significant activity were then concentrated again using a PM 10 ultrafiltration membrane and then equilibrated in 50 mM phosphate pH 7.0 buffer containing 0.5 M $(NH_4)_2SO_4$.

The concentrated sample was then loaded onto a Phenyl Superose column pre-equilibrated with 50 mM phosphate pH 7.0 buffer containing 0.5 M $(NH_4)_2SO_4$. The enzyme was eluted with a gradient from 0.5 M ammonium sulfate containing 50 mM phosphate buffer to 50 mM phosphate buffer containing no ammonium sulfate. Active fractions were pooled.

SDS-PAGE analysis of the purified aminopeptidase revealed one band with a molecular weight of 67 kDa. The purified aminopeptidase was designated *Sphingomonas capsulata* aminopeptidase I.

Example 23

Purification of *Sphingomonas capsulata* Aminopeptidase I from Crude Enzyme Powder The crude enzyme powder described in Example 21 was dissolved in distilled water and loaded onto a CM Sepharose CL-6B column (Pharmacia Biotech, Uppsala, Sweden) pre-equilibrated with 15 mM sodium phosphate buffer pH 6.0 buffer. Aminopeptidase I activity was eluted with a linear gradient of 15 mM to 60 mM sodium phosphate buffer (pH 6.0). Fractions of 7.4 ml are collected and assayed for aminopeptidase activity as described in Example 22.

Active fractions were pooled and dialyzed against 15 mM phosphate pH 6.0 buffer. The dialysate was sequentially loaded onto a hydroxylapatite column equilibrated with 15 mM sodium phosphate pH 6.0 buffer. Aminopeptidase I activity was eluted with a linear gradient of 15 mM to 300 mM sodium phosphate 6.0 buffer. Fractions were collected and assayed for aminopeptidase activity. Active fractions were pooled, dialyzed against distilled water, and lyophilized.

Example 24

Purification of *Sphingomonas capsulata* Aminopeptidase I

*Sphingomonas capsulata* aminopeptidase I was purified from a culture broth supernatant produced by cultivation of *Sphingomonas capsulata* strain IFO 12533 for 15 hours at 31° C., 250 rpm, and an initial pH of 7.45 in 1.5 liters of medium composed of per liter 10 g of bactopeptone, 5 g of yeast extract, 3 g of NaCl, 2 g of $K_2HPO_4$, 0.1 g of $MgSO_4$—$7H_2O$, and 5 g of glucose (autoclaved separately).

Aminopeptidase I activity was measured with alanine-para-nitroanilide (Ala-pNA) as described in Example 22.

The culture broth supernatant (approximately 1 liter) prepared by centrifugation, filtered using a Whatman glass microfiber filter (Whatman, Maidstone, England), filtered using Nalgene Filterware equipped with a 0.22 mm filter, and concentrated using an Amicon Spiral Ultrafiltration System (Amicon, New Bedford, Mass., USA), was equilibrated with 10 mM sodium phosphate pH 6.0 buffer until the conductivity and pH were equal to the loading buffer, 50 mM MES pH 6.0. The filtered solution was loaded onto a 24×390 mm column containing approximately 180 ml of SP-Sepharose, Fast Flow (Pharmacia Biotech AB, Uppsala, Sweden) pre-equilibrated with 50 mM MES pH 6.0 buffer. Protein with aminopeptidase I activity was eluted with a 240 ml gradient from 0 to 0.2M NaCl in 50 mM MES pH 6.0 buffer. Fractions with aminopeptidase I activity were pooled, desalted using a DIAFLO™ PM 10 ultrafiltration membrane (Amicon, New Bedford, Mass., USA), and equilibrated with 20 mM sodium phosphate pH 7.0 buffer.

The pooled solution was then loaded onto a Pharmacia MonoQ Beads column pre-equilibrated with 20 mM sodium phosphate pH 7.0 buffer. Protein with aminopeptidase I activity did not bind to the column and was collected in the flow-through. The flow-through was concentrated using a PM 10 membrane system as above, and the pH adjusted to 6.0 with 70 mM sodium acetate pH 4.0 buffer.

The concentrated flow-through was loaded onto a Pharmacia Mono S column pre-equilibrated with 50 mM MES pH 6.0 buffer. The aminopeptidase was eluted with a 60 ml gradient from 0 to 0.2 M NaCl in 50 mM MES pH 6.0 buffer. The fractions with significant Ala-pNA activity were then pooled, concentrated, and equilibrated with 50 mM phosphate pH 7.0 buffer containing 0.5 M $(NH_4)_2SO_4$ using a PM 10 membrane system as above.

Finally, the concentrated sample was loaded onto a Pharmacia Phenyl Superose 5/5 pre-packed 7×50 mm column (Pharmacia Biotech AB, Uppsala, Sweden) pre-equilibrated with 50 mM phosphate pH 7.0 buffer containing 0.5 M $(NH_4)_2SO_4$. Protein with aminopeptidase I activity was then eluted with a 30 ml gradient from 0.5 to 0 M $(NH_4)_2SO_4$ in 50 mM phosphate pH 7.0 buffer. Fractions containing aminopeptidase I activity were analyzed by SDS-PAGE and then pooled.

SDS-PAGE analysis of the purified Sphingomonas capsulata aminopeptidase I revealed one band with a molecular weight of 67 kDa.

Example 25

Amino Acid Sequencing of *Sphingomonas capsulata* Aminopeptidase I (67 kDa)

A 20 μl sample of the purified *Sphingomonas capsulata* aminopeptidase I described in Example 22 was electrophoresed and subsequently blot-transferred to a PVDF membrane using 10 mM CAPS (3-[cyclohexylamino]-1-propanesulfonic acid) pH 11 in 10% methanol for 2 hours. The PVDF membrane was stained with 0.1% Coommassie Blue R-250 in 40% methanol/1% acetic acid for 20 seconds and destained in 50% ethanol to observe the protein bands. The major band of 67 kDa was excised and subjected to amino terminal sequencing on an Applied Biosystems Model 476A Protein Sequencer using a blot cartridge and liquid phase TFA delivery according to the manufacturers instructions. The protein was found to be N-terminally blocked to Edman sequencing chemistry.

A 1.0 ml sample of the purified aminopeptidase I described in Example 22 was dried on a Savant Speed Vac AS160 and then reconstituted with 300 μl of 70% formic acid (aqueous). A few crystals of cyanogen bromide were added and incubated at room temperature in the dark overnight. The sample was redried in the Speed Vac and reconstituted in Tricine sample buffer (Novex, San Diego, Calif., USA). The cyanogen bromide cleavage fragments were separated using a 10–20% Tricine SDS-polyacrylamide gel into bands of 42, 30, 17, 15, 10, 6, and 4 kDa and blot-transferred to a PVDF membrane. The 6, 10, 15, 17, 30, and 42 kDa bands were excised and subjected to amino terminal sequencing. The N-terminal sequence of the 10 kDa band was determined to contain the following sequence while the N-terminal sequences of the other bands were inconclusive: AVNGDAYDADKLKGAITNAKTGNPGAGRPI (SEQ ID NO. 11).

Example 26

Characterization of *Sphingomonas capsulata* Aminopeptidase I (67 kDa)

Stock solutions of 100 mg of each para-nitroanilide per ml of dimethylsulfoxide were diluted with 50 mM sodium phosphate pH 7.5 buffer to concentrations of 2 mg per ml. Where the substrates were incompletely soluble, their suspensions were used (shown with an asterisk in Table 9 below). The reaction of the *Sphingomonas capsulata* aminopeptidase I with each para-nitroanilide was initiated when a 10 µl aliquot of the enzyme solution in 50 mM sodium phosphate pH 7.0 was added to 190 µl of a substrate solution in a 96 well microtiter plate. Analysis of initial rates of hydrolysis of the para-nitroanilides was monitored at 405 nm and 25° C. in a THERMOmax Microplate Reader (Molecular Devices Corp., Sunnyvale, Calif., USA). The results (Table 9) showed that the aminopeptidase I preferably hydrolyzed Ala-pNA, but also hydrolyzed Gly-pNA. However, among the dipeptide substrates the aminopeptidase I hydrolysed Gly-Phe-pNA more quickly than Ala-Ala-pNA.

TABLE 9

Substrate specificity of *Sphingomonas capsulata* aminopeptidase I

| Amino acid p-nitroanilides | Relative activity (%) |
|---|---|
| Ala | 100 |
| Met | 24 |
| Gly* | 20 |
| Leu | 18.5 |
| Glu* | 6 |
| Asp | 4.5 |
| Lys | 6 |
| Ile | 0.5 |
| Val | 0.5 |
| Phe* | 0 |
| Pro | 0 |

The pH optimum for the 67 kDa aminopeptidase was determined using the following protocol. The buffer solutions at different pH's were prepared by adding distilled water to 4.25 g of sodium acetate and 3.78 g of Tris (free base) to a final volume of 250 ml and adjusting the pH to 8.5, 8.0, 7.5, 7.0, 6.5, 5.80, 5.5, and 5.0 with 36.5–38% HCl. Aliquots of 10 ml were removed at each pH. A 20 µl volume of a 100 mg/ml solution of Ala-pNA in DMSO was added to 980 µl of each buffer solution. The pH was then determined to be 8.5, 8.0, 7.57, 7.30, 7.09, 6.68, 6.14, and 5.25 for the buffer solutions after the addition of the substrate. Another solution of substrate at a concentration of 2 mg/ml was prepared at the various pH's. The reaction was initiated by the addition of 10 µl of enzyme solution, diluted 5-fold in 10 mM Tris-HCl pH 7.5, to 200 µl of substrate at the various pHs at room temperature and monitored at 405 nm.

Figure 6:
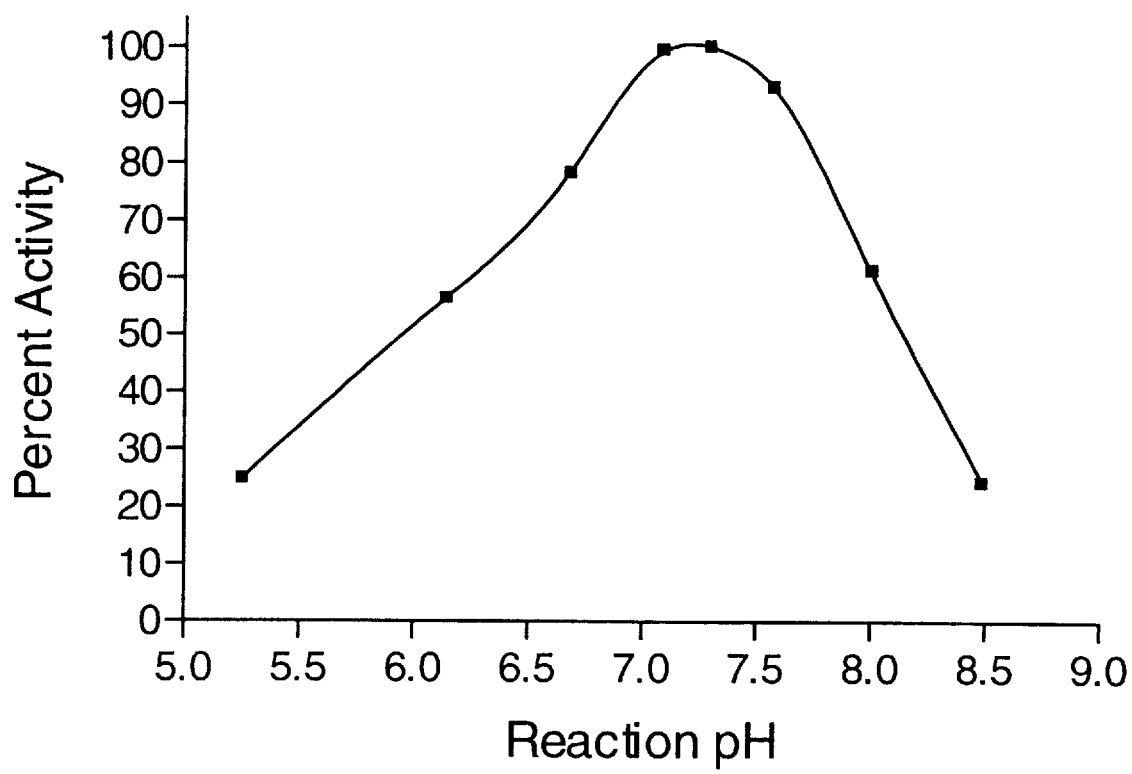
FIG. 6 shows the activity of a *Sphingomonas capsulata* aminopeptidase versus pH measured at room temperature using a 100 mg/ml solution of Ala-pNA in DMSO.

The results shown in Table 10 demonstrated that aminopeptidase I has a pH optimum in the range of 5.3 to 8.5, and more preferably in the range of 7.0 to 7.5 (see FIG. 6). There was no detectable autohydrolysis of Ala-pNa in the pH range 5.25–8.5. At pH 5.5, hydrolysis of Ala-pNA catalyzed by aminopeptidase I did not follow Michaelis-Menten kinetics where the apparent $K_m$ and $V_{max}$ had negative values due to the activation of the enzyme by a substrate. At pH 7.5, the $K_m$ was 2.5 mM.

TABLE 10 pH profile of *Sphingomonas capsulata* aminopeptidase I

| pH | Relative Activity (%) |
|---|---|
| 5.25 | 24.9 |
| 6.14 | 56.4 |
| 6.68 | 78.4 |
| 7.09 | 99.4 |
| 7.30 | 100 |
| 7.57 | 92.8 |
| 8.0 | 61 |
| 8.49 | 24.2 |

Figure 7:
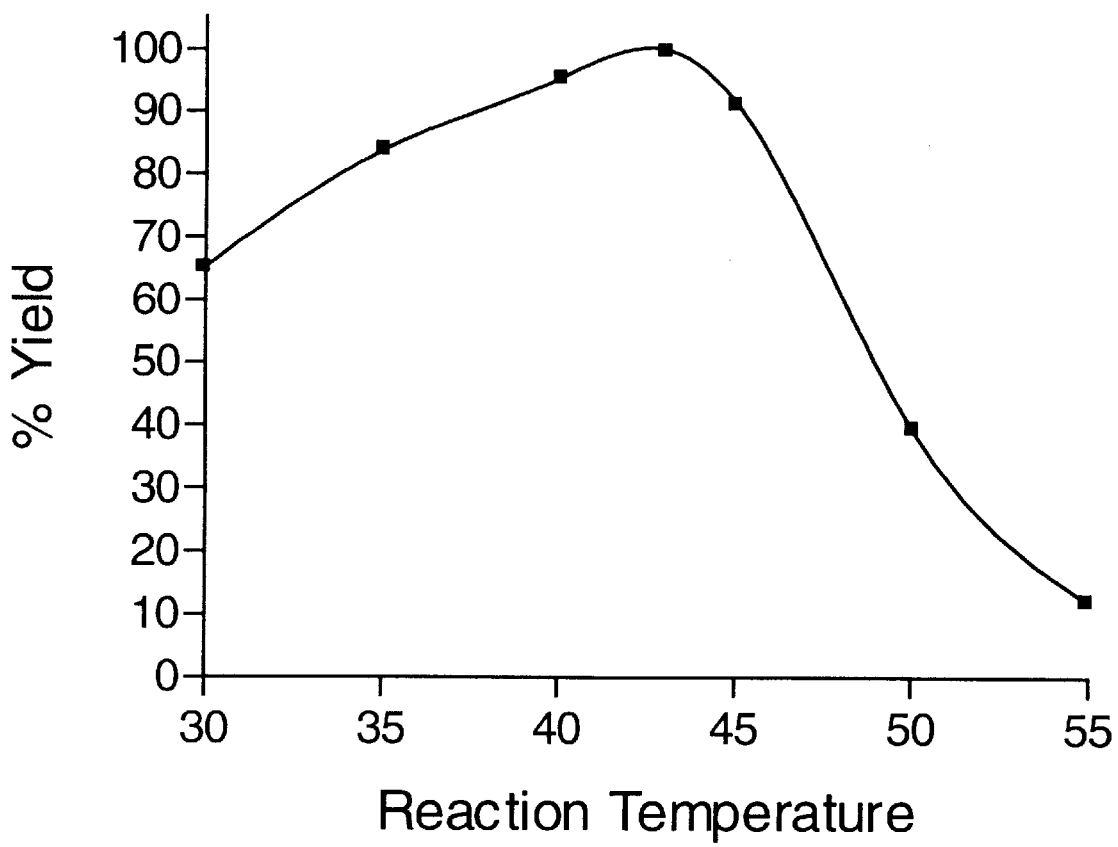
FIG. 7 shows the activity of a *Sphingomonas capsulata* aminopeptidase versus the temperature in 50 mM sodium phosphate buffer pH 7.5.

The temperature optimum was determined using Ala-pNA as substrate in 50 mM sodium phosphate pH 7.5 buffer over the temperature range of 30° C. to 55° C. The results showed that aminopeptidase I has a temperature optimum in the range of 35° C. to 46° C., and more preferably in the range of 40° C. to 45° C. at pH 7.5 (see FIG. 7).

Figure 8:
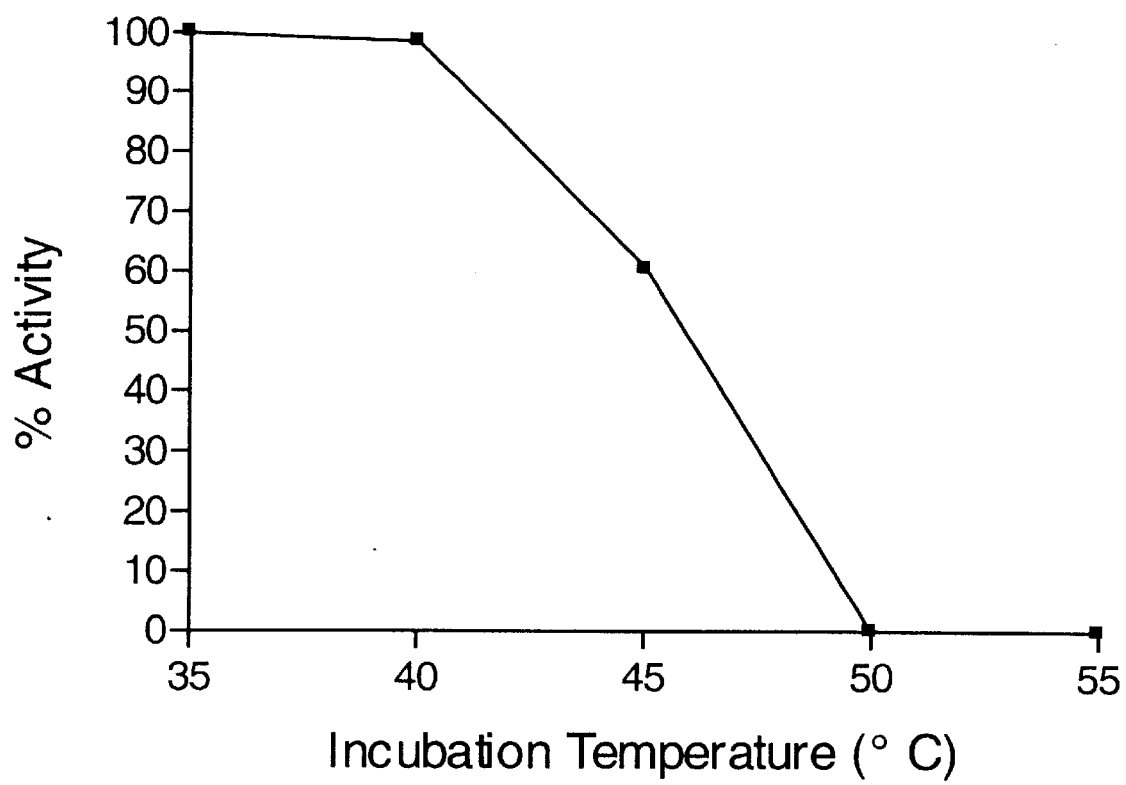
FIG. 8 shows the activity of a *Sphingomonas capsulata* aminopeptidase versus the temperature in 50 mM sodium phosphate buffer pH 7.5.

The temperature stability of aminopeptidase I was determined by incubating the enzyme for 20 minutes in 50 mM sodium phosphate pH 7.5 buffer at temperatures in the range of 35° C. to 55° C. followed by cooling on ice and measuring the residual activity using Ala-pNA as substrate at pH 7.5 as described above. The results showed (see FIG. 8) that the aminopeptidase was approximately 100% stable up to 40° C. at pH 7.5. At 45° C., the enzyme retained approximately 60% residual activity, while at 50° C. the enzyme was completely inactivated.

Example 27

Comparison Between DH Increasing Effect of Crude and Purified *Sphingomonas capsulata* Aminopeptidase I The DH increasing effect of *Sphingomonas capsulata* aminopeptidase I (67 kDa) was evaluated in soy protein hydrolysis and compared to the performance of the crude enzyme powder prepared as described in Example 21.

The degree of hydrolysis (DH) of the soy protein was determined as follows. The DH, defined as described in by Adler-Nissen (1986, *Enzymic Hydrolysis of Food Proteins*, Elsevier Applied Science Publishers), was determined by reaction of the supernatant with OPA (ortho-phtaldialdehyde, Sigma Chemical Co., St. Louis, Mo.) essentially as described by Church et al., 1983, *Journal of Dairy Science* 66: 1219–1227 with correction factors as determined by Adler-Nissen, 1979, *Agricultural and Food Chemistry* 27: 1256–1262.

The aminopeptidase I was added in increasing dosage to either a low background (1.5% of the substrate protein) or a high background (6% of the substrate protein) of FLA-VOURZYME 1000L™ and a dosage of ALCALASE 2.4L® of 1.5% of the substrate protein. The experiments were carried out as described below:

Hydrolysis was carried out on a 10 ml scale at 50° C. for 18 hours. The initial pH was 7 with no pH readjustment during hydrolysis. Inactivation of the enzyme was carried out at 85° C. for 3 minutes in a water bath. The substrate concentration was 2% protein from soy bean meal. The substrate was heat treated in a water bath at 85° C. for 3 minutes. The enzymes used were FLAVOURZYME 1000L™, ALCALASE 2.4L®, crude enzyme powder (see Example 21), and the purified *Sphingomonas capsulata* aminopeptidase I described in Example 24.

The aminopeptidase dosages used were based on alanyl-aminopeptidase units (AAU) determined by the hydrolysis of Ala-pNa at pH 7.5. One AAU unit of the aminopeptidase I is defined as the quantity of an enzyme which hydrolyses 1.0 micromole of Ala-pNa per minute in a 9.1 mM solution of Ala-pNa at pH 7.5, 22° C., and ionic strength 50 mM.

The specific activity of the purified aminopeptidase I was approximately 12 AAU/mg enzyme. Therefore, a dosage of 0.24 AAU per 200 mg soy protein, for example, corresponded to 0.1 g enzyme per kg soy protein.

Figure 9:
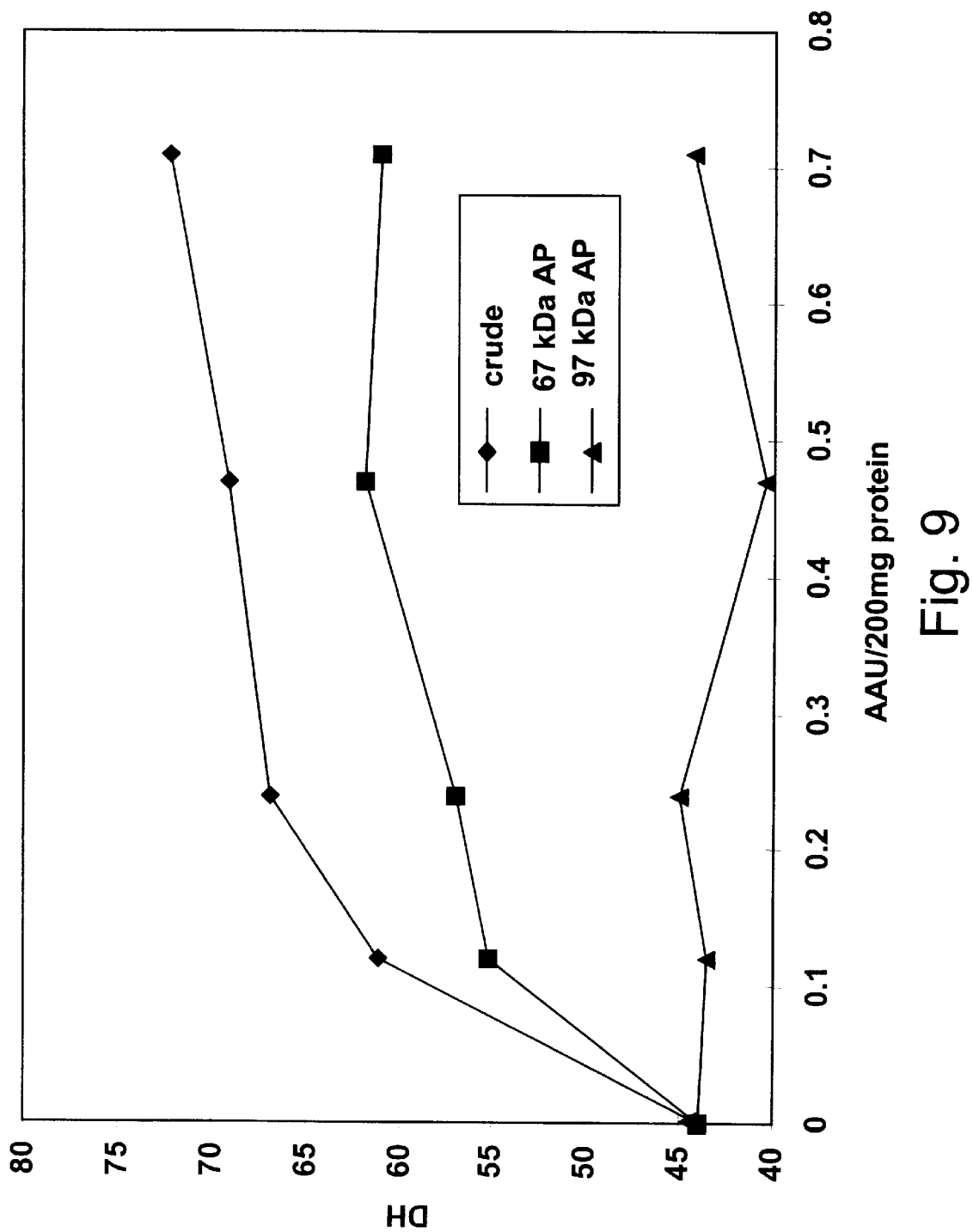
FIG. 9 shows the effect on the DH when adding a *Sphingomonas capsulata* crude enzyme extract and a *Sphingomonas capsulata* aminopeptidase to respectively low and high Flavourzyme™ background dosage.
Figure 10:
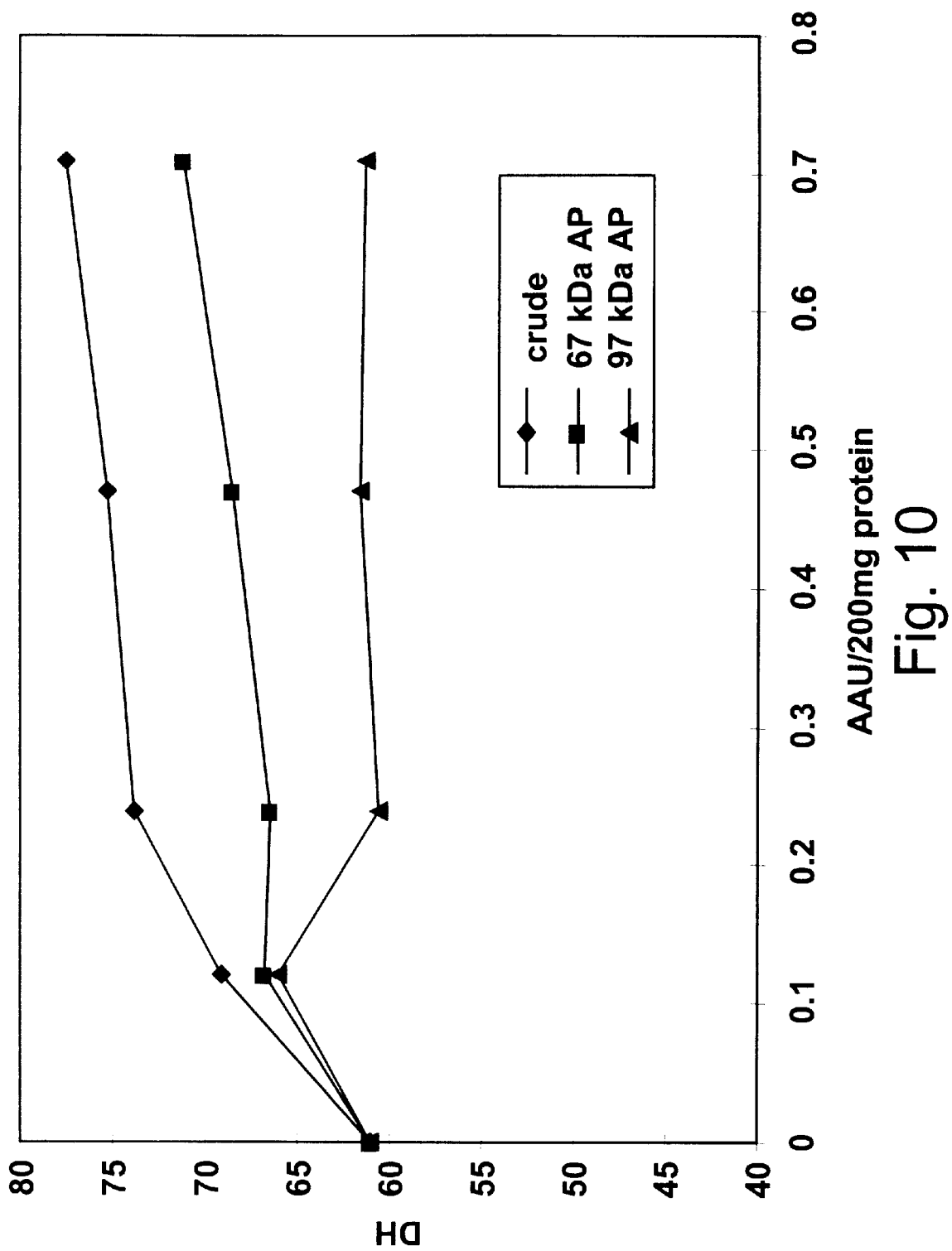
FIG. 10 shows the effect on the DH when adding a *Sphingomonas capsulata* crude enzyme extract and a *Sphingomonas capsulata* aminopeptidase to respectively low and high Flavourzyme™ background dosage.

The DH as function of dosage of AAU is shown in FIG. 9 for low background dosages of FLAVOURZYME™ and in FIG. 10 for a high background dosage of FLAVOURZYME™.

FIGS. 9 and 10 show that the hydrolysates were close to being saturated with AAU at the highest dosages of AAU. The crude enzyme was capable of increasing DH from 44% to 72% when added to a low dosage of FLAVOURZYME™. The purified aminopeptidase I increased DH to 61–62%. Thus, the purified aminopeptidase I was responsible for (62−44)/(72−44)×100%=64% of the DH increasing effect of the crude enzyme. The crude enzyme increased DH from 61% to 77% when added to a high dosage of FLAVOURZYME™. The purified aminopeptidase I increased DH to 71%. Thus, the purified aminopeptidase I was responsible for (71−61)/(77−61)×100%=63% of the increasing effect of the crude enzyme.

An alternative to addition of aminopeptidase I is the addition of more FLAVOURZYME™. The addition of 0.5% extra FLAVOURZYME™ to the background dosage of 1.5% increased DH from 44% to 48%. The effect of adding aminopeptidase I was calculated to be (62−48)/(72−48)×100%=58% of the effect of the crude enzyme.

Likewise, addition of 1% extra FLAVOURZYME™ to the background dosage of 6% FLAVOURZYME™ increased DH from 61% to 63%. The effect of the aminopeptidase I was calculated to be (71−63)/(77−63)×100%=57% of the effect of the crude enzyme.

The highest DH obtained was 77%. Since the DH value was based on total protein and not on soluble protein, the protein solubility was around 85%. Therefore, DH in the soluble protein was around 91%, which was very close to 100%.

Example 28

Free Amino Acid Analysis

The % relative increase in the individual free amino acids (FAA) due to AAU additions are shown in Table 11. Hyp, methioninsulphonic acid, and Trp were not included in the Table due to very fluctuating and uncertain results.

TABLE 11

% Relative increase in FAA due to addition of aminopeptidases

| FAA | 1.5% FLAVOURZYME™ + crude | 1.5% FLAVOURZYME™ + 67 kDa AP | 6.0% FLAVOURZYME™ + crude | 6.0% FLAVOURZYME™ + 67 kDa AP | 1.5% FLAVOURZYME™ + 67 kDa AP versus 6.0% FLAVOURZYME™ |
|---|---|---|---|---|---|
| Asp | 250.3 | 164.5 | 74.8 | 24.8 | 24.2 |
| Glu | 195.6 | 145.9 | 70.7 | 31.3 | 28.7 |
| Asn | 80.5 | 32.3 | 36.9 | 7.6 | −15.2 |
| Ser | 149.5 | 69.3 | 78.7 | 41.7 | 12.5 |
| Gln | 198.6 | 138.9 | 51.6 | 28.1 | 9.9 |
| Gly | 353.6 | 305.7 | 117.4 | 92.9 | 90.6 |
| His | 64.0 | 30.3 | 18.8 | 7.5 | −6.8 |
| Arg | 59.6 | 37.4 | 18.1 | −31.4 | −2.9 |
| Thr | 84.3 | 34.7 | 21.2 | 2.4 | −18.3 |
| Ala | 200.2 | 130.3 | 71.2 | 36.5 | 27.3 |
| Pro | 73.2 | 32.4 | −9.0 | −11.5 | −39.7 |
| Tyr | 75.4 | 47.6 | 13.8 | 8.5 | −6.9 |
| Val | 114.1 | 44.0 | 32.5 | 6.3 | −17.7 |
| Met | 47.9 | −20.0 | 42.5 | 21.1 | −46.7 |
| Cys | 5.0 | 12.6 | 17.5 | 9.5 | 6.3 |
| Ile | 133.6 | 48.7 | 34.0 | 7.2 | −21.0 |
| Leu | 67.4 | 35.2 | 16.4 | 5.2 | −9.1 |
| Phe | 62.6 | 41.8 | 13.3 | 7.2 | −4.5 |
| Lys | 105.5 | 62.4 | 28.2 | 13.8 | −1.4 |
| total | 110.1 | 64.5 | 36.9 | 10.3 | 0.0 |
| DH | 59.6 | 34.8 | 24.4 | 14.2 | −2.2 |

The results showed that when the crude or purified *Sphingomonas capsulata* aminopeptidase I was added, Gly was the amino acid which showed the highest increase. Other amino acids, which showed increased release were Ala, Glu, Gln, Asp and Ser, but for these amino acids the crude enzyme appeared to release more than the purified aminopeptidase I alone probably due to the presence of other aminopeptidases in the crude enzyme.

A high DH hydrolysate was produced by use of a high dosage of FLAVOURZYME™. The same high DH and release of FAA were obtained by using a low dosage of FLAVOURZYME™ supplemented with 67 kDa aminopeptidase I or the crude enzyme. According to Table 12, a hydrolysate obtained by use of a low dosage of FLAVOURZYME™ supplemented with 67 kDa aminopeptidase I will have a higher level of especially Gly, but also Ala, Glu and Asp and a lower level of Met, Pro and Ile as compared with hydrolysates obtained by using a high dosage of FLAVOURZYME™ alone.

Example 29

DH Increasing Effect of *Sphingomonas capsulata* Aminopeptidase I in Gelatin Hydrolysis The DH increasing effect of the *Sphingomonas capsulata* aminopeptidase I was tested in gelatin hydrolysis.

The aminopeptidase I was added in increased dosage to either a low or a high background of FLAVOURZYME™ and ALCALASE® as performed in Example 27.

Hydrolysis was carried out in 200 µl reactions in Eppendorf tubes. The substrate gelatin (Merck) was dissolved in distilled water at 85° C. for 5 minutes. After cooling to 50° C., the pH was adjusted to 6.5. The final gelatin concentration was adjusted to 2% after the addition of enzymes. The substrate concentration in each reaction was calculated to be 4 mg.

The enzymes used were FLAVOURZYME™, ALCALASE®, crude enzyme powder, purified aminopeptidase I. Glycine aminopeptidase unit (GAPU) of both crude and purified enzyme was measured in 50 mM Tris-HCl pH 7.5 buffer at 37° C. using Gly-pNA as a substrate. Aminopeptidase I was assayed at 37° C. in 50 mM Tris-HCl (pH 7.5). Gly-pNA (Bachem Feinchemikalien AG, Bubendorf, Switzerland) was dissolved in 40% dioxane at a concentration of 2.5 mg/ml and 1.5 volume of 50 mM Tris-HCl (pH 7.5) was added to a substrate concentration of 1 mg/ml. The enzyme sample was diluted in 500 µl of the same buffer and 100 µl of the substrate solution was added and incubated at 37° C. for 5 minutes. The reaction was terminated by the addition of 300 µl of 1 M sodium acetate pH 4.0 buffer. For the blank reaction, the stop solution was added to the enzyme solution and incubated for 5 minutes at 37° C., and then the substrate solution was added. The absorbance at 410 nm was measured for both the sample and blank reactions. The enzyme activity was calculated using the molecular extinction coeficient at 410 nm for pNA as 9480 $M^{-1}$ $cm^{-1}$. One unit of GAPU was defined as the quantity of enzyme that hydrolyses 1 micromole of Gly-pNA at 37° C. per minute under the conditions described above. The specific activities of the crude and purified aminopeptidase I used were 0.725 GAPU/mg and 6.45 GAPU/mg, respectively. The enzymes were dosed to the 4 mg protein according to the scheme in Table 12.

Enzyme/substrate ratios are given in parentheses after amounts of enzymes shown as weight.

The hydrolysis reactions were performed at 50° C. for 18 hours. Enzymes were inactivated at 85° C. for 5 minutes followed by centrifugation. DH was calculated on the basis of the total protein content of hydrolysate using the OPA method.

Figure 11:
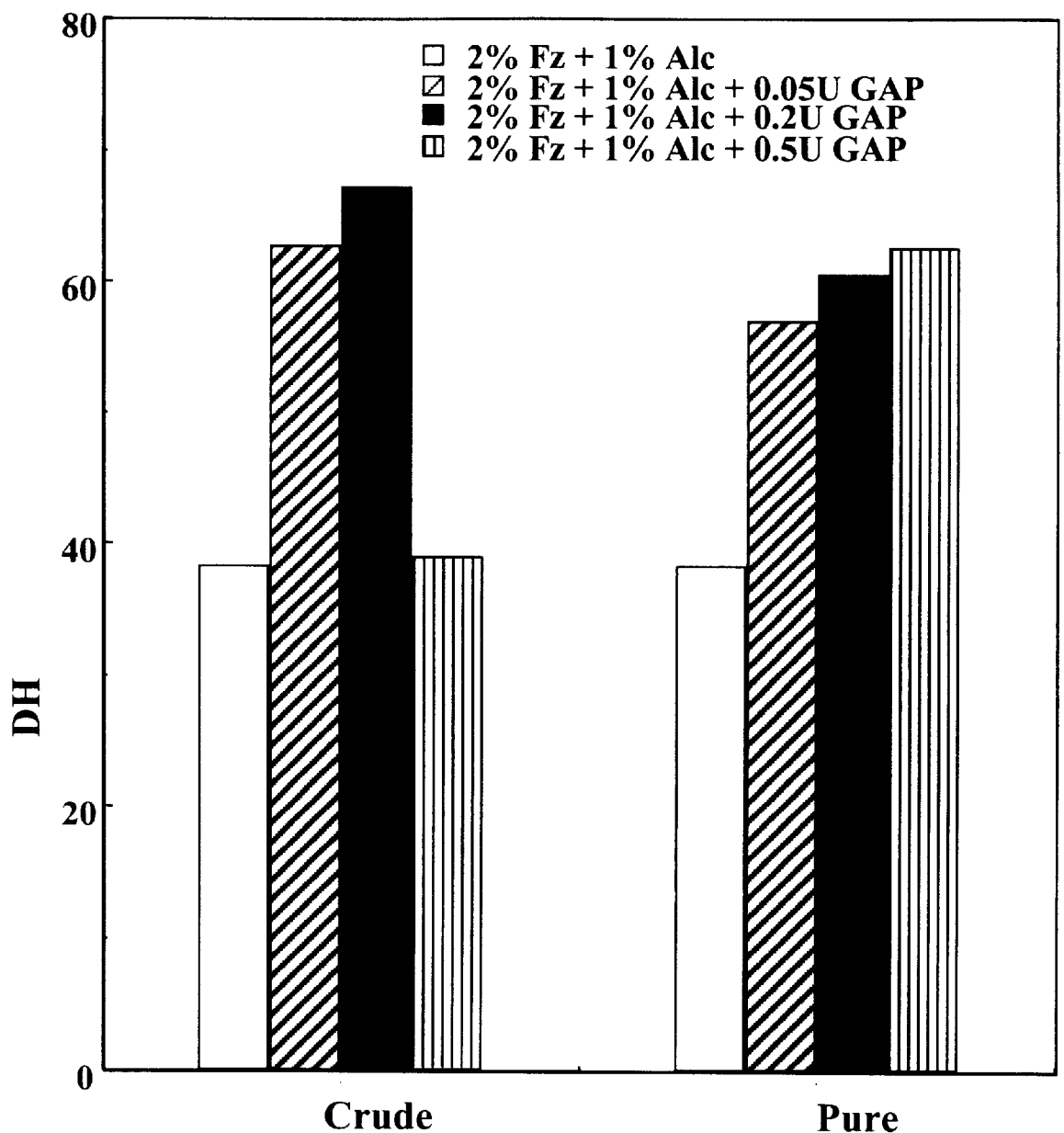
FIG. 11 shows the DH obtained by different combinations of Flavourzyme™, Alcalase® and a *Sphingomonas capsulata* aminopeptidase.
Figure 12:
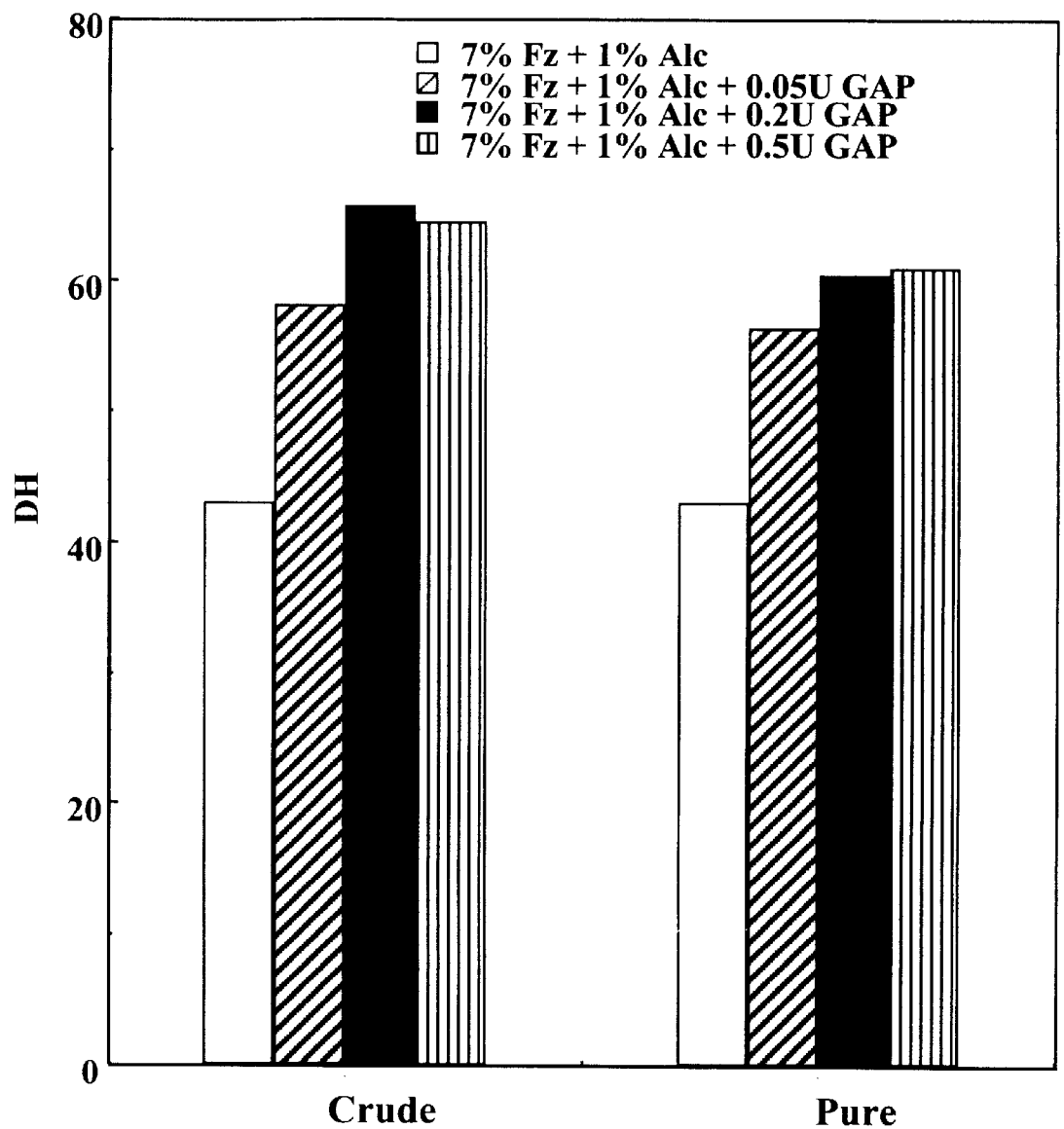
FIG. 12 shows the DH obtained by different combinations of Flavourzyme™, Alcalase® and a *Sphingomonas capsulata* aminopeptidase.

The DH-increasing effect of purified aminopeptidase I shown in FIGS. 11 and 12 demonstrated that addition of the crude and the purified enzyme (0.2 U/4 mg gelatin) to the low FLAVOURZYME™ background increased DH from 38% to 67% and 61%, respectively. The DH increasing effect was almost saturated at this dose.

When the dose of FLAVOURZYME™ was increased up to 7%, the control DH increased to 43%. However, the DH obtained with purified aminopeptidase I was 61% which almost coincided with those obtained in the low FLAVOURZYME™ background.

These results indicated that the *Sphingomonas capsulata* aminopeptidase I hydrolyses proteins to an extremely high DH. Furthermore, using aminopeptidase I, the dosage of other proteolytic enzymes can be reduced to obtain the same DH.

TABLE 12

| Tube no. | FLAVOURZYME™ (µg) | ALCALASE® (µg) | Aminopeptidase I (µg) |
|---|---|---|---|
| 1 | 80 (2%) | 40 (1%) | |
| 2 | 80 (2%) | 40 (1%) | |
| 3 | 80 (2%) | 40 (1%) | |
| 4 | 80 (2%) | 40 (1%) | |
| 5 | 80 (2%) | 40 (1%) | 8 (0.2%)≈0.05 U |
| 6 | 80 (2%) | 40 (1%) | 31 (0.77%)≈0.2 U |
| 7 | 80 (2%) | 40 (1%) | 78 (2%)≈0.5 U |
| 8 | 80 (2%) | 40 (1%) | 155 (4%)≈1.0 U |
| 9 | 280 (7%) | 40 (1%) | |
| 10 | 280 (7%) | 40 (1%) | |
| 11 | 280 (7%) | 40 (1%) | |
| 12 | 280 (7%) | 40 (1%) | |
| 13 | 280 (7%) | 40 (1%) | 8 (0.2%)≈0.05 U |
| 14 | 280 (7%) | 40 (1%) | 31 (0.77%)≈0.2 U |
| 15 | 280 (7%) | 40 (1%) | 78 (2%)≈0.5 U |
| 16 | 280 (7%) | 40 (1%) | 155 (4%)≈1.0 U |

Deposit of Biological Materials

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
|---|---|---|
| *E. coli* DH5α pEJG18 | NRRL B-21677 | April 4, 1997 |

---

What is claimed is:

1. A method of producing a protein hydrolysate, comprising adding to a proteinaceous material one or more polypeptides having glycine-releasing activity and one or more additional proteases wherein the amount of glycine produced is greater than the amount of glycine produced by the one or more additional proteases alone under the same conditions. wherein the one or more polypeptides having glycine-releasing activity are obtained from an Aspergillus and/or Sphingomonas strain selected from the group consisting of:

(a) a polypeptide having an amino acid sequence which has at least 90% identity with SEQ ID NO. 2 or SEQ ID NO. 11;

(b) a polypeptide encoded by a nucleic acid sequence which hybridizes under medium stringency conditions with (i) the nucleic acid sequence of SEQ ID NO. 1 or SEQ ID NO. 10, or (ii) its complementary strand, wherein medium stringency conditions are defined as prehybridization and hybridization at 42° C. in 5×SSPE, 0.3% SDS, 200 μg/ml sheared and denatured salmon sperm DNA, and 35% formamide;

(c) a fragment of (a) or (b), wherein the fragment has aminopeptidase activity;

(d) a polypeptide having aminopeptidase activity with physicochemical properties of (i) a pH optimum in the range of about pH 7.27 to about pH 10.95 determined at ambient temperature in the presence of Ala-para-nitroanilide; (ii) a temperature stability of 90% or more, relative to initial activity, at pH 7.5 determined after incubation for 20 minutes at 60° C. in the absence of substrate; and (iii) aminopeptidase activity against Xaa-para-nitroanilide wherein Xaa is selected from the group consisting of Leu, Glu, Gly, Ala, and Pro; and (e) a polypeptide having aminopeptidase activity with physicochemical properties of (i) a pH optimum in the range of about pH 5.0 to about 8.5 measured at 37° C., (ii) an isoelectric point in the range of 7.4–8.5; (iii) has aminopeptidase activity in the temperature range of 20–55° C., measured at pH 7.5 using Gly-pNA in Tris-HCl buffer; (iv) hydrolyzes Ala-pNA, Gly-pNA, Leu-pNA, Glu-pNA, Asp-pNA, Lys-pNA, Ile-pNA and Val-pNA; (e) does not hydrolyze Phe-pNA or Pro-pNA; and (v) is not inhibited by phenylmethanesulfonyl fluoride, and completely inhibited by o-phenanthroline.

2. The method of claim 1, wherein the percent increase of glycine is between about 25% to about 400%.

3. The method of claim 1, wherein the degree of hydrolysis is between about 35% to about 90%.

4. The method of claim 1, wherein the polypeptide having glycine-releasing activity has an amino acid sequence which has at least 95% identity with SEQ ID NO. 2 or SEQ ID NO. 11.

5. The method of claim 4, wherein the polypeptide having glycine-releasing activity has an amino acid sequence which has at least 97% identity with SEQ ID NO. 2 or SEQ ID NO. 11.

6. The method of claim 1, wherein the polypeptide having glycine-releasing activity has an amino acid sequence of SEQ ID NO. 2 or SEQ ID NO. 11.

7. The method of claim 1, wherein the polypeptide having glycine-releasing activity is encoded by a nucleic acid sequence which hybridizes under high stringency conditions with (i) the nucleic acid sequence of SEQ ID NO. 1 or SEQ ID NO. 10, or (ii) its complementary strand, wherein high stringency conditions are defined as prehybridization and hybridization at 42° C. in 5×SSPE, 0.3% SDS, 200 μg/ml sheared and denatured salmon sperm DNA, and 50% formamide.

8. The method of claim 1, wherein the polypeptide is obtained from an *Aspergillus oryzae* strain.

9. The method of claim 8, wherein the *Aspergillus oryzae* strain is *Aspergillus oryzae* ATCC 20386.

10. The method of claim 1, wherein the polypeptide is obtained from a *Sphingomonas capsulata* strain.

11. The method of claim 10, wherein the *Sphingomonas capsulata* strain is *Sphingomonas capsulata* IFO 12533.

12. The method of claim 1, wherein the one or more additional proteases are endopeptidases.

13. The method of claim 12, wherein the endopeptidase is a glutamyl endopeptidase (EC 3.4.21.19); lysyl endopeptidase (EC 3.4.21.50); leucyl endopeptidase (EC 3.4.21.57); glycyl endopeptidase (EC 3.4.22.25); proly endopeptidase (EC 3.4.21.26); trypsin (EC 3.4.21.4), lysine/arginine-specific endopeptidase; or peptidyl-aspartate metalloendopeptidase (EC 3.4.24.33).

14. The method of claim 1, wherein the one or more additional proteases are an exo-peptidase that may act from either end of the peptde.

15. The method of claim 14, wherein the exopeptidase is an aminopeptidase.

16. The method of claim 15, wherein the aminopeptdase is a leucyl aminopeptidase (EC 3.4.11.1), dipeptidyl aminopeptidase, or tripeptide aminopeptidase (EC 3.4.11.4).

17. The method of claim 14, wherein the exopeptidase is a carboxypeptidase.

18. The method of claim 17, wherein the carboxypeptidase is a proline carboxypeptidase (EC 3.4.16.2); carboxypeptidase A (EC 3.4.17.1); carboxypeptidase B (EC 3.4.17.2); carboxypeptidase C (EC 3.4.16.5); carboxypeptidase D (EC 3.4.16.6); lysine (arginine) carboxypeptidase (EC 3.4.17.3); glycine cartoxypeptidase (EC 3.4.17.4); an alanine carboxypeptidase (EC 3.4.17.6); glutamate carboxypeptidase (EC 3.4.17.11); peptidyl-dipeptidase A (EC 3.4.15.1); or peptidyl dipeptidase (EC 3.4.15.5).

19. The method of claim 2, wherein the one or more additional proteases is a mixture of proteases obtained from *Aspergillus oryzae* strain ATCC 20386.

20. The method of claim 2, further comprising adding to the proteinaceouus material one or more other enzymes selected from the group consisting of amylase, carbohydrase, cellulase, esterase, alpha-galactosidase, beta-galactosidase, glucoamylase, alpha-glucosidase, beta-glucosidase, lipase, pectinolytic enzyme, peptidoglutaminase, phytase, transglutaminase, and xylanase.

21. The method of claim 2, wherein the proteineceous material is a foodstuff of animal origin.

22. The method of claim 21, wherein the foodstuff of animal origin is milk protein, whey protein, casein, meat protein, fish protein, blood protein, or egg white gelatin.

23. The method of claim 2, wherein the proteineceous material is a foodstuff of vegetable origin.

24. The method of claim 23, wherein the foodstuff of vegetable origin is soy, grain, cotton seed, rape seed, peanut, alfalfa, pea, fabaceous bean, sesame seed, or sunflower protein.

* * * * *

SEQUENCE LISTING

<160> NUMBER OF SEQ ID NOS: 11

<210> SEQ ID NO 1
<211> LENGTH: 1491
<212> TYPE: DNA
<213> ORGANISM: Aspergillus oryzae

<400> SEQUENCE: 1

```
atgaggtcgc ttttgtgggc ttcgttgctt tcgggcgtgt tggctgggag ggcgcttgtt      60
tcgccggatg agttccccga ggatattcag ttggaagatc tgctggaagg atcccaacag     120
cttgaggact tcgcctatgc ctaccccgag cgcaatcgcg tctttggtgg taaagcccac     180
gacgacacgg ttaactatct ctacgaggag ctgaagaaga ctggctacta tgatgtctac     240
aagcagcctc aggtgcacct gtggagcaat gccgaccaga cgctcaaggt gggcgatgag     300
```

-continued

```
gaaatcgagg cgaagaccat gacctacagt cccagcgtcg aggtcaccgc cgatgtagcc    360
gtcgtcaaga acctgggatg cagcgaggcg gattacccat ccgatgtcga gggcaaggtc    420
gccctgatca agcgtggaga atgcccgttc ggcgacaagt cggttctcgc tgccaaagcc    480
aaggccgcgg cttcgattgt ctataacaat gtggccggat ccatggcggg cacccttggc    540
gcggcgcaga gtgataaggg accgtattcg gccattgtcg gtatcagctt ggaggatggc    600
cagaagctga tcaagcttgc tgaggctgga tcggtatctg tggatctgtg ggtggatagt    660
aagcaggaga accgtacgac gtataacgtt gtcgcgcaga cgaagggcgg cgatccgaac    720
aacgtcgtcg cgctgggtgg ccacacggac tcagtcgagg cgggccctgg tatcaacgac    780
gatggctcgg gcattattag caacttggtc attgccaaag cgctcacgca gtactccgtc    840
aagaatgccg tgcgcttcct cttctggaca gcagaggagt tcggtctgct gggcagcaac    900
tactacgtct cccatctgaa tgccaccgag ctgaacaaga tccgactgta cctgaacttc    960
gacatgatcg cctcacctaa ctacgccctc atgatctatg acggtgatgg atcggcgttc   1020
aaccagagcg gaccggccgg ttccgcccag atcgagaaac tgttcgagga ctactacgac   1080
tccatcgacc tgcctcatat ccccacccag tttgacggac gttccgacta cgaggccttt   1140
atcctgaacg gcattccgtc cggtggactc ttcacgggcg ccgagggcat catgtccgaa   1200
gagaacgcaa gccgctgggg aggtcaagcc ggcgtggcct acgacgccaa ctaccacgcc   1260
gcgggagaca acatgaccaa cctcaaccat gaagccttcc tgatcaactc caaagccacc   1320
gccttcgccg tcgccaccta cgccaacgac ctctcctcga tccccaaacg gaataccaca   1380
tcctccttgc accgacgagc ccgcaccatg cgaccattcg gcaagagagc tccgaagaca   1440
cacgctcacg tatcaggatc cggatgctgg cattctcaag tcgaggcata g            1491
```

<210> SEQ ID NO 2
<211> LENGTH: 496
<212> TYPE: PRT
<213> ORGANISM: Aspergillus oryzae

<400> SEQUENCE: 2

```
Met Arg Ser Leu Leu Trp Ala Ser Leu Leu Ser Gly Val Leu Ala Gly
  1               5                  10                  15

Arg Ala Leu Val Ser Pro Asp Glu Phe Pro Asp Ile Gln Leu Glu
                 20                  25                  30

Asp Leu Leu Glu Gly Ser Gln Gln Leu Glu Asp Phe Ala Tyr Ala Tyr
             35                  40                  45

Pro Glu Arg Asn Arg Val Phe Gly Gly Lys Ala His Asp Asp Thr Val
         50                  55                  60

Asn Tyr Leu Tyr Glu Glu Leu Lys Lys Thr Gly Tyr Tyr Asp Val Tyr
 65                  70                  75                  80

Lys Gln Pro Gln Val His Leu Trp Ser Asn Ala Asp Gln Thr Leu Lys
                 85                  90                  95

Val Gly Asp Glu Glu Ile Glu Ala Lys Thr Met Thr Tyr Ser Pro Ser
            100                 105                 110

Val Glu Val Thr Ala Asp Val Ala Val Lys Asn Leu Gly Cys Ser
            115                 120                 125

Glu Ala Asp Tyr Pro Ser Asp Val Glu Gly Lys Val Ala Leu Ile Lys
        130                 135                 140

Arg Gly Glu Cys Pro Phe Gly Asp Lys Ser Val Leu Ala Ala Lys Ala
145                 150                 155                 160

Lys Ala Ala Ala Ser Ile Val Tyr Asn Asn Val Ala Gly Ser Met Ala
```

```
                    165                 170                 175
        Gly Thr Leu Gly Ala Ala Gln Ser Asp Lys Gly Pro Tyr Ser Ala Ile
                    180                 185                 190
        Val Gly Ile Ser Leu Glu Asp Gly Gln Lys Leu Ile Lys Leu Ala Glu
                    195                 200                 205
        Ala Gly Ser Val Ser Val Asp Leu Trp Val Asp Ser Lys Gln Glu Asn
                    210                 215                 220
        Arg Thr Thr Tyr Asn Val Val Ala Gln Thr Lys Gly Asp Pro Asn
        225                 230                 235                 240
        Asn Val Ala Leu Gly Gly His Thr Asp Ser Val Glu Ala Gly Pro
                    245                 250                 255
        Gly Ile Asn Asp Asp Gly Ser Gly Ile Ile Ser Asn Leu Val Ile Ala
                    260                 265                 270
        Lys Ala Leu Thr Gln Tyr Ser Val Lys Asn Ala Val Arg Phe Leu Phe
                    275                 280                 285
        Trp Thr Ala Glu Glu Phe Gly Leu Leu Gly Ser Asn Tyr Tyr Val Ser
                    290                 295                 300
        His Leu Asn Ala Thr Glu Leu Asn Lys Ile Arg Leu Tyr Leu Asn Phe
        305                 310                 315                 320
        Asp Met Ile Ala Ser Pro Asn Tyr Ala Leu Met Ile Tyr Asp Gly Asp
                    325                 330                 335
        Gly Ser Ala Phe Asn Gln Ser Gly Pro Ala Gly Ser Ala Gln Ile Glu
                    340                 345                 350
        Lys Leu Phe Glu Asp Tyr Tyr Asp Ser Ile Asp Leu Pro His Ile Pro
                    355                 360                 365
        Thr Gln Phe Asp Gly Arg Ser Asp Tyr Glu Ala Phe Ile Leu Asn Gly
                    370                 375                 380
        Ile Pro Ser Gly Gly Leu Phe Thr Gly Ala Glu Gly Ile Met Ser Glu
        385                 390                 395                 400
        Glu Asn Ala Ser Arg Trp Gly Gln Ala Gly Val Ala Tyr Asp Ala
                    405                 410                 415
        Asn Tyr His Ala Ala Gly Asp Asn Met Thr Asn Leu Asn His Glu Ala
                    420                 425                 430
        Phe Leu Ile Asn Ser Lys Ala Thr Ala Phe Ala Val Ala Thr Tyr Ala
                    435                 440                 445
        Asn Asp Leu Ser Ser Ile Pro Lys Arg Asn Thr Thr Ser Ser Leu His
        450                 455                 460
        Arg Arg Ala Arg Thr Met Arg Pro Phe Gly Lys Arg Ala Pro Lys Thr
        465                 470                 475                 480
        His Ala His Val Ser Gly Ser Gly Cys Trp His Ser Gln Val Glu Ala
                    485                 490                 495

<210> SEQ ID NO 3
<211> LENGTH: 20
<212> TYPE: PRT
<213> ORGANISM: Aspergillus oryzae

<400> SEQUENCE: 3

Cys Cys Ile Gly Ala Tyr Gly Ala Arg Thr Thr Tyr Cys Cys Ile Gly
1               5                   10                  15

Ala Arg Gly Ala
            20

<210> SEQ ID NO 4
<211> LENGTH: 36
```

-continued

```
<212> TYPE: PRT
<213> ORGANISM: Aspergillus oryzae

<400> SEQUENCE: 4

Arg Thr Thr Tyr Thr Thr Ile Ala Cys Ile Ala Cys Ile Gly Cys Ile
 1               5                  10                  15

Ala Cys Arg Thr Cys Ile Gly Cys Ile Gly Thr Ile Ala Cys Tyr Thr
            20                  25                  30

Cys Ile Ala Cys
        35

<210> SEQ ID NO 5
<211> LENGTH: 537
<212> TYPE: PRT
<213> ORGANISM: Saccharomyces cerevisiae

<400> SEQUENCE: 5

Met His Phe Ser Leu Lys Gln Leu Ala Val Ala Ala Phe Tyr Ala Thr
 1               5                  10                  15

Asn Leu Gly Ser Ala Tyr Val Ile Pro Gln Phe Phe Gln Glu Ala Phe
            20                  25                  30

Gln Gln Glu Glu Pro Ile Glu Asn Tyr Leu Pro Gln Leu Asn Asp Asp
        35                  40                  45

Asp Ser Ser Ala Val Ala Ala Asn Ile Pro Lys Pro His Ile Pro Tyr
    50                  55                  60

Phe Met Lys Pro His Val Glu Ser Glu Lys Leu Gln Asp Lys Ile Lys
65                  70                  75                  80

Val Asp Asp Leu Asn Ala Thr Ala Trp Asp Leu Tyr Arg Leu Ala Asn
                85                  90                  95

Tyr Ser Thr Pro Asp Tyr Gly His Pro Thr Arg Val Ile Gly Ser Lys
            100                 105                 110

Gly His Asn Lys Thr Met Glu Tyr Ile Leu Asn Val Phe Asp Asp Met
        115                 120                 125

Gln Asp Tyr Tyr Asp Val Ser Leu Gln Glu Phe Glu Ala Leu Ser Gly
    130                 135                 140

Lys Ile Ile Ser Phe Asn Leu Ser Asp Ala Glu Thr Gly Lys Ser Phe
145                 150                 155                 160

Ala Asn Thr Thr Ala Phe Ala Leu Ser Pro Pro Val Asp Gly Phe Val
                165                 170                 175

Gly Lys Leu Val Glu Ile Pro Asn Leu Gly Cys Glu Gly Lys Asp Tyr
            180                 185                 190

Ala Ser Val Val Pro Pro Arg His Asn Glu Lys Gln Ile Ala Leu Ile
        195                 200                 205

Glu Arg Gly Lys Cys Pro Phe Gly Asp Lys Ser Asn Leu Ala Gly Lys
    210                 215                 220

Phe Gly Phe Thr Ala Val Ile Tyr Asp Asn Glu Pro Lys Ser Lys
225                 230                 235                 240

Glu Gly Leu His Gly Thr Leu Gly Glu Pro Thr Lys His Thr Val Ala
                245                 250                 255

Thr Val Gly Val Pro Tyr Lys Val Gly Lys Lys Leu Ile Ala Asn Ile
            260                 265                 270

Ala Leu Asn Ile Asp Tyr Ser Leu Tyr Phe Ala Met Asp Ser Tyr Val
        275                 280                 285

Glu Phe Ile Lys Thr Gln Asn Ile Ile Ala Asp Thr Lys His Gly Asp
    290                 295                 300
```

```
Pro Asp Asn Ile Val Ala Leu Gly Ala His Ser Asp Ser Val Glu Glu
305                 310                 315                 320

Gly Pro Gly Ile Asn Asp Asp Gly Ser Gly Thr Ile Ser Leu Leu Asn
            325                 330                 335

Val Ala Lys Gln Leu Thr His Phe Lys Ile Asn Asn Lys Val Arg Phe
            340                 345                 350

Ala Trp Trp Ala Ala Glu Glu Gly Leu Leu Gly Ser Asn Phe Tyr
        355                 360                 365

Ala Tyr Asn Leu Thr Lys Glu Glu Asn Ser Lys Ile Arg Val Phe Met
370                 375                 380

Asp Tyr Asp Met Met Ala Ser Pro Asn Tyr Glu Tyr Glu Ile Tyr Asp
385                 390                 395                 400

Ala Asn Asn Lys Glu Asn Pro Lys Gly Ser Glu Glu Leu Lys Asn Leu
                405                 410                 415

Tyr Val Asp Tyr Tyr Lys Ala His His Leu Asn Tyr Thr Leu Val Pro
            420                 425                 430

Phe Asp Gly Arg Ser Asp Tyr Val Gly Phe Ile Asn Asn Gly Ile Pro
            435                 440                 445

Ala Gly Gly Ile Ala Thr Gly Ala Glu Lys Asn Asn Val Asn Asn Gly
450                 455                 460

Lys Val Leu Asp Arg Cys Tyr His Gln Leu Cys Asp Asp Val Ser Asn
465                 470                 475                 480

Leu Ser Trp Asp Ala Phe Ile Thr Asn Thr Lys Leu Ile Ala His Ser
            485                 490                 495

Val Ala Thr Tyr Ala Asp Ser Phe Glu Gly Phe Pro Lys Arg Glu Thr
            500                 505                 510

Gln Lys His Lys Glu Val Asp Ile Leu Asn Ala Gln Gln Pro Gln Phe
        515                 520                 525

Lys Tyr Arg Ala Asp Phe Leu Ile Ile
530                 535
```

<210> SEQ ID NO 6
<211> LENGTH: 23
<212> TYPE: DNA
<213> ORGANISM: Artificial Sequence
<220> FEATURE:
<223> OTHER INFORMATION: Aspergillus oryzae

<400> SEQUENCE: 6
atgatgaggt cgcttttgtg ggc                23

<210> SEQ ID NO 7
<211> LENGTH: 23
<212> TYPE: DNA
<213> ORGANISM: Artificial Sequence
<220> FEATURE:
<223> OTHER INFORMATION: Aspergillus oryzae

<400> SEQUENCE: 7
gggatgcatc tatgcctcga ctt                23

<210> SEQ ID NO 8
<211> LENGTH: 32
<212> TYPE: DNA
<213> ORGANISM: Artificial Sequence
<220> FEATURE:
<223> OTHER INFORMATION: Aspergillus oryzae

<400> SEQUENCE: 8

-continued atttaaatca ccatgaggtc gcttttgtgg gc                                           32

<210> SEQ ID NO 9
<211> LENGTH: 32
<212> TYPE: DNA
<213> ORGANISM: Artificial Sequence
<220> FEATURE:
<223> OTHER INFORMATION: Aspergillus oryzae

<400> SEQUENCE: 9
gggttaatta actatgcctc gacttgagaa tg                                           32

<210> SEQ ID NO 10
<211> LENGTH: 1926
<212> TYPE: DNA
<213> ORGANISM: Sphingomonas capsulata

<400> SEQUENCE: 10
caggtgcagc cggcgagcaa cagccgcccg atggcagtgc cgatcgctca tggggtgccc            60
gatgcgcagg acgtgcccta tcccggcacg atcgggctgc agatcgatgc caccgatctg           120
gccaccgggg cgttccgggt ggtggaaacc gtgccggtgg cggccgatgc caaggaactg           180
atcctgcaac tgccggcctg gctgccgggt gagcatggca atcgcggccc cgtggccgag           240
ctggccggca tcacgtttga agccaagggc cagaagctgg cctggacccg cgacccggtg           300
gaagtgaacg cgttccacat cccctgccc gccggcacca gcgaagtggt ggcccgcttc            360
atccacacct cgccgctgcg cgacagcgaa ggccgcatca ccgttacgcg cgaaatgctc           420
aacgtgcagt gggagaagat gagcctctat cccgccggtc actatgtgcg gcagatcaag           480
gtgcgtccca ccgtcagctt cccgcagggt tggaccgtgt tcaccgcgct ggatggcaag           540
acgcagagcg gcgcgggcaa taccgtgact tgggccgaaa ccgactatga aaccctggtc           600
gattcgccga tctttgccgg gctctatgcc gcgcggcatg atctgggcca caacgtctat           660
ttcgatctgg tggccgacaa gcccgagctg ctggcgatca agccggaaaa cctggccgcc           720
tatcgcaacc tggccgacga agccgtgggc gcattcggcg cgcgccattt cgatcactac           780
gatttcctgc tcgcgctgac cgatcgcatg ggcagcatcg gcctggaaca ccaccgttcc           840
agcgaaaacc agcaggaacc caagagcctg accgactggg ccgcctatga ctgggaccgc           900
aacgtgatcg cccacgaatt cagccacagc tgggatggca agtatcgccg ctcggccaag           960
ctgtggacgc ccgactatcg ccagccgatg caggacaacc tgctgtgggt ctatgaaggg          1020
cagacgcagt tctggggcct ggtcctggcc gcacgctcgg gcgtgcagag caaggacgtg          1080
gtcttgggca gcctcgccaa ctatgccggc acgttcaccc agaccgccgg gcgcgactgg          1140
cgctcggtgg aagacacgac gatggatccc atcttcgccg cccgcaagcc caagccctat          1200
tcctcgctta cccgtaacga ggactattac accgaaggcg cgctggtgtg gctggaagcg          1260
gaccagatca tccgcgatgg caccggcggc aagaagggcc tggatgattt cgccaaggcg          1320
ttctttggcg tgcgcgacgg cgattgggc gtgctgacct atgaattcga tgacgtggtc           1380
aagaccctca acgcgtctat cccctatgac tgggccacgt tcctcaagac ccgcctgcag          1440
acgccgggcc agcggtgcc gctcggcggg atcgagcgcg cggctacaa gctggaattc           1500
aaggacgagc ccaaccccta tgacaaggcg cgcatggccg atgccaaggt gctcagcctg          1560
ttcaactcgc tgggcgtgac gctggacaag gacggcaaag tcaccgcctc gcgctgggat          1620
ggcccggcgt tcaaggcggg gctggtttcg gcatgcagg tgatgccgt gaacggcgac            1680
gcctatgacg cggacaagct caagggcgcg atcaccaatg ccaagaccgg caaccccggc          1740

-continued

```
gccggccgcc cgatcgaact gctggtcaag cgtgacgatc gctttgtcac gctgccgatc    1800
acctatgccg atggcctgcg ctggccgtgg ctggtgcgca cggcgccggg cacggcaccg    1860
accgggctgg acaagctgct ggccccgcac gccagcaagc tgcccgtggg caaggctgcc    1920
aagtga                                                               1926
```

<210> SEQ ID NO 11
<211> LENGTH: 673
<212> TYPE: PRT
<213> ORGANISM: Sphingomonas capsulata

<400> SEQUENCE: 11

```
Met Arg Lys Thr Pro Gln Gly Ile Gly Leu Leu Ser Ala Leu Ser Thr
 1               5                  10                  15

Ser Thr Leu Ala Leu Ala Thr Leu Ile Leu Ala Gln Pro Ala Leu Ala
            20                  25                  30

Val Gln Pro Ala Ser Asn Ser Arg Pro Met Ala Val Pro Ile Ala
        35                  40                  45

His Gly Val Pro Asp Ala Gln Asp Val Pro Tyr Pro Gly Thr Ile Gly
    50                  55                  60

Leu Gln Ile Asp Ala Thr Asp Leu Ala Thr Gly Ala Phe Arg Val Val
65                  70                  75                  80

Glu Thr Val Pro Val Ala Ala Asp Ala Lys Glu Leu Ile Leu Gln Leu
                85                  90                  95

Pro Ala Trp Leu Pro Gly Glu His Gly Asn Arg Gly Pro Val Ala Glu
            100                 105                 110

Leu Ala Gly Ile Thr Phe Glu Ala Lys Gly Gln Lys Leu Ala Trp Thr
        115                 120                 125

Arg Asp Pro Val Glu Val Asn Ala Phe His Ile Pro Leu Pro Ala Gly
    130                 135                 140

Thr Ser Glu Val Val Ala Arg Phe Ile His Thr Ser Pro Leu Arg Asp
145                 150                 155                 160

Ser Glu Gly Arg Ile Thr Val Thr Arg Glu Met Leu Asn Val Gln Trp
                165                 170                 175

Glu Lys Met Ser Leu Tyr Pro Ala Gly His Tyr Val Arg Gln Ile Lys
            180                 185                 190

Val Arg Pro Thr Val Ser Phe Pro Gln Gly Trp Thr Val Phe Thr Ala
        195                 200                 205

Leu Asp Gly Lys Thr Gln Ser Gly Ala Gly Asn Thr Val Thr Trp Ala
    210                 215                 220

Glu Thr Asp Tyr Glu Thr Leu Val Asp Ser Pro Ile Phe Ala Gly Leu
225                 230                 235                 240

Tyr Ala Ala Arg His Asp Leu Gly His Asn Val Tyr Phe Asp Leu Val
                245                 250                 255

Ala Asp Lys Pro Glu Leu Leu Ala Ile Lys Pro Glu Asn Leu Ala Ala
            260                 265                 270

Tyr Arg Asn Leu Ala Asp Glu Ala Val Gly Ala Phe Gly Ala Arg His
        275                 280                 285

Phe Asp His Tyr Asp Phe Leu Leu Ala Leu Thr Asp Arg Met Gly Ser
    290                 295                 300

Ile Gly Leu Glu His His Arg Ser Ser Glu Asn Gln Gln Glu Pro Lys
305                 310                 315                 320

Ser Leu Thr Asp Trp Ala Ala Tyr Asp Trp Asp Arg Asn Val Ile Ala
                325                 330                 335
```

```
His Glu Phe Ser His Ser Trp Asp Gly Lys Tyr Arg Arg Ser Ala Lys
            340             345             350

Leu Trp Thr Pro Asp Tyr Arg Gln Pro Met Gln Asp Asn Leu Leu Trp
            355             360             365

Val Tyr Glu Gly Gln Thr Gln Phe Trp Gly Leu Val Leu Ala Ala Arg
            370             375             380

Ser Gly Val Gln Ser Lys Asp Val Val Leu Gly Ser Leu Ala Asn Tyr
385             390             395             400

Ala Gly Thr Phe Thr Gln Thr Ala Gly Arg Asp Trp Arg Ser Val Glu
            405             410             415

Asp Thr Thr Met Asp Pro Ile Phe Ala Ala Arg Lys Pro Lys Pro Tyr
            420             425             430

Ser Ser Leu Thr Arg Asn Glu Asp Tyr Tyr Thr Glu Gly Ala Leu Val
            435             440             445

Trp Leu Glu Ala Asp Gln Ile Ile Arg Asp Gly Thr Gly Gly Lys Lys
            450             455             460

Gly Leu Asp Asp Phe Ala Lys Ala Phe Phe Gly Val Arg Asp Gly Asp
465             470             475             480

Trp Gly Val Leu Thr Tyr Glu Phe Asp Val Val Lys Thr Leu Asn
            485             490             495

Gly Val Tyr Pro Tyr Asp Trp Ala Thr Phe Leu Lys Thr Arg Leu Gln
            500             505             510

Thr Pro Gly Gln Pro Val Pro Leu Gly Gly Ile Glu Arg Gly Gly Tyr
            515             520             525

Lys Leu Glu Phe Lys Asp Glu Pro Asn Pro Tyr Asp Lys Ala Arg Met
            530             535             540

Ala Asp Ala Lys Val Leu Ser Leu Phe Asn Ser Leu Gly Val Thr Leu
545             550             555             560

Asp Lys Asp Gly Lys Val Thr Ala Ser Arg Trp Asp Gly Pro Ala Phe
            565             570             575

Lys Ala Gly Leu Val Ser Gly Met Gln Val Met Ala Val Asn Gly Asp
            580             585             590

Ala Tyr Asp Ala Asp Lys Leu Lys Gly Ala Ile Thr Asn Ala Lys Thr
            595             600             605

Gly Asn Pro Gly Ala Gly Arg Pro Ile Glu Leu Leu Val Lys Arg Asp
            610             615             620

Asp Arg Phe Val Thr Leu Pro Ile Thr Tyr Ala Asp Gly Leu Arg Trp
625             630             635             640

Pro Trp Leu Val Arg Thr Ala Pro Gly Thr Ala Pro Thr Gly Leu Asp
            645             650             655

Lys Leu Leu Ala Pro His Ala Ser Lys Leu Pro Val Gly Lys Ala Ala
            660             665             670

Lys
```